US006384055B1

(12) United States Patent
Merce-Vidal et al.

(10) Patent No.: US 6,384,055 B1
(45) Date of Patent: May 7, 2002

(54) UTILIZATION OF DERIVATIVES OF TETRAHYDROPYRIDINES (OR 4-HYDROXYPIPERIDINES)-BUTYLAZOLS IN THE PREPARATION OF A MEDICAMENT FOR THE TREATMENT OF PAIN

(75) Inventors: Ramon Merce-Vidal; Jordi Frigola-Constansa, both of Barcelona (ES)

(73) Assignee: Laboratorios Del Dr. Esteves, S.A., Barcelona (ES)

( * ) Notice: Subject to any disclaimer, the term of this patent is extended or adjusted under 35 U.S.C. 154(b) by 0 days.

(21) Appl. No.: 09/743,085

(22) PCT Filed: Jul. 9, 1999

(86) PCT No.: PCT/ES99/00222

§ 371 Date: Feb. 13, 2001

§ 102(e) Date: Feb. 13, 2001

(87) PCT Pub. No.: WO00/02519

PCT Pub. Date: Jan. 20, 2000

(30) Foreign Application Priority Data

Jul. 10, 1998 (ES) .............................................. 9801467

(51) Int. Cl.[7] ...................... A61K 31/445; A61K 31/44; C07D 211/06; C07D 401/00

(52) U.S. Cl. ........................ 514/326; 514/340; 514/341; 514/343; 546/205; 546/208; 546/210; 546/268.4; 546/272.7

(58) Field of Search ................................. 514/326, 340, 514/341, 343; 546/210, 208, 205, 268.4, 272.7

(56) References Cited

FOREIGN PATENT DOCUMENTS

| | | | |
|---|---|---|---|
| WO | 9604287 | 2/1996 | ................. 546/326 |
| WO | 9735584 | 10/1997 | ................. 546/326 |

*Primary Examiner*—Alan L. Rotman
*Assistant Examiner*—Raymond Covington
(74) *Attorney, Agent, or Firm*—Ladas & Parry

(57) ABSTRACT

Derivatives of tetrahydropyridines (or 4-hydroxypiperidines)-butylazols of formula (I), wherein $R_1$, $R_2$ and $R_3$, which are similar or different, represent each of them hydrogen, halogen, alkyl $C_1$–$C_4$, trifluoromethyl, hydroxyl, alkoxyl, or two adjacent radicals can form a ring; A is a C atom and the dotted line represents an additional bond, or A is a C atom joined to a hydroxyl group and the dotted line represents absence of additional bond; $Z_1$ is N or CR4; $Z_2$ is N or $CR_5$; $Z_4$ is N or $CR_7$; and $R_4$, $R_5$, $R_6$ and $R_7$, which different, represent hydrogen, halogen, alkyl $C_1$–$C_4$, aryl or substituted aryl, or two adjacent radicals can form part of another ring. These derivatives are useful for the treatment of acute pain, neuropathic pain or nociceptive pain in mammals, including human beings.

7 Claims, No Drawings

UTILIZATION OF DERIVATIVES OF TETRAHYDROPYRIDINES (OR 4-HYDROXYPIPERIDINES)-BUTYLAZOLS IN THE PREPARATION OF A MEDICAMENT FOR THE TREATMENT OF PAIN

FIELD OF THE INVENTION

The present invention relates to the use of derivatives of tetrahydropyridines (or 4-hydroxypyperidines)butylazoles of general formula (I), as well as their physiologically acceptable salts, in the preparation of medicaments useful in human and/or veterinary therapy for the treatment of acute pain, neuropathic pain and nociceptive pain, either alone or in combination with other analgesics, producing in this case a synergy.

BACKGROUND OF THE INVENTION

In our patent application WO 96/04287 compounds of general formula (I) are disclosed (I)

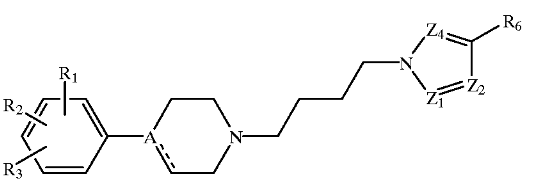

that have an affinity for the cy and $5HT_{1A}$ receptors, and which are claimed as medicaments useful for the treatment of anxiety, psychosis, epilepsy, convulsion, amnesia, cerebro-vascular diseases and senile dementia.

We have now discovered that the compounds of general formula (I), as well as their pharmaceutically acceptable salts, are especially useful for the preparation of medicaments, useful in human and/or veterinary therapy for the prophylaxis, alleviation or curing of acute pain, neuropathic pain and nociceptive pain, either alone or in combination with other analgesics, giving rise in this case to a synergy.

DETAILED DESCRIPTION OF THE INVENTION

The present invention relates to the use of derivatives of tetrahydropyridines (or 4-hydroxypyperidine)butylazoles of general formula:

(I)

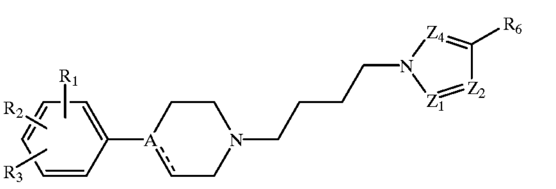

where $R_1$, $R_2$ and $R_3$ are either identical or different and represent a hydrogen atom, a $C_1$–$C_4$ alkyl group, a trifluoromethyl radical, a hydroxyl or alkoxyl radical, and furthermore, two adjacent radicals can form part of an six-member aromatic ring; A represents a carbon atom and the dotted line represents an additional bond, or A represents a carbon atom bound to a hydroxyl group (C—OH) and the dotted line represents the lack of an additional bond;

$Z_1$ represents a nitrogen atom or a substituted carbon atom that can be represented by C—$R_4$;

$Z_2$ represents a nitrogen atom or a substituted carbon atom that can be represented by C—$R_5$;

Z4 represents a nitrogen atom or a substituted carbon atom that can be represented by C—$R_7$;

with the condition that $Z_1$, $Z_2$ and $Z_4$ taken together can represent, at most, two nitrogen atoms; and $R_4$, $R_5$, $R_6$ and $R_7$, are identical or different and represent a hydrogen atom, a halogen atom, a $C_1$–$C_4$ alkyl group, an aryl or substituted aryl group, or two adjacent radicals can form part of a six-member aromatic ring;

or one of their physiologically acceptable salts, in the elaboration of a medicament for the treatment of acute pain, neuropatic pain or nocipeptive pain in mammals, including man.

The term "a halogen atom" represents a fluorine, chlorine or bromine atom.

The term "aryl or substituted aryl" represents a phenyl radical or a phenyl radical substituted by halogen.

The term "alkoxyl" represents a methoxyl or ethoxyl radical.

The term "$G_1$–$G_4$ alkyl" represents a straight chain or branched radical that is based on a saturated hydrocarbon of 1 to 4 atoms of carbon, such as methyl, ethyl, propyl, isopropyl, butyl, isobutyl, sec-butyl y tercbutyl for example.

Physiologically acceptable salts of the compounds of general formula (I) refer both to salts formed with inorganic acids and organic acids, in particular, to salts of hydrochloric acid, hydrobromic acid, sulphuric acid, phosphoric acid, acetic acid, lactic acid, malonic acid, succinic acid, glutaric acid, fumaric acid, malic acid, tartaric acid, citric acid, ascorbic acid, maleic acid, benzoic acid, phenylacetic acid, cinamic acid, salicylic acid and alkyl, cycloalkyl or arylsulphonic acids.

The use of derivatives of general formula (I) for the treatment of pain refers to the use of analgesics in clinical practice. The term acute pain includes, but is not limited to, headache, arthritis, muscular tension or dysmenorrhea. The term neuropathic pain includes, but is not limited to, chronic back pains, pain associated with arthritis, herpes, pain associated with cancer, pain of a phantom limb, pain during childbirth or neuropathic pain resistant to opoids. The term nociceptive pain includes, but is not limited to, post-operation pain, dental pain, pain arising from surgery, pain caused by serious burns, post-natal pain or pain related with the genitourinary tract.

The derivatives of general formula (I) can be prepared according to the procedures disclosed in our patent application WO 96/04287.

In human therapy, the dosage administered of the compounds of the present invention varies as a function of the seriousness of the affliction to be treated. Normally the dosage will lie between 1 and 100 mg/day. The compounds of the invention can be administered as the only active ingredient or in conjunction with another analgesic in 2 proportion of one part of compound of general formula (I) with around one to ten parts of the other analgesic, with the aim of provoking a synergy. Other analgesics include, but are not limited to, non-steroid anti-inflammatory compounds such as aspirin or indomethacine, other analgesics such as paracetamol, narcotic analgesics or related compounds such as morphine, meperidine or pentazocine. The compounds of the invention, with a suitable pharmaceutical formulation, are administered by different routes, such as orally, transdermically, parenterally, subcutaneously, intranasally, intramuscularly or intravenously. Pharmaceutical compositions that contain compounds of general formula (I) are disclosed in our patent application WO 96/04287.

Illustrative examples of compounds included in the scope of the present invention include compounds that are characterised by the data indicated in tables 1 and 2.

TABLE 1

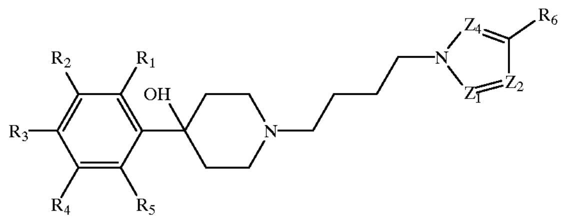

| Ex. | $R_1$ | $R_2$ | $R_3$ | $R_4$ | $R_5$ | $Z_1$ | $Z_2$ | $R_6$ | $Z_4$ | m.p. | IR $cm^{-1}$ | $^1$H-RMN (300 MHz), δ (solvent) |
|---|---|---|---|---|---|---|---|---|---|---|---|---|
| 1 | H | H | H | H | H | N | CH | Cl | CH | 102–103° C. | 3364 (b.a., OH), 2950, 2810, 1375, 1130, 991, 969, 760, 696, 605 KBr | 1.56(quin, J=7.1Hz, 2H), 1.65(b.a., 1H); 1.76 (d, J=12.4Hz, 2H); 1.90(quin, J=7.6Hz, 2H); 2.20(m, 2H); 2.40–2.55(a.c., 4H); 2.83(d, J=9.5Hz, 2H); 4.11 (t, JH=8Hz, 2H); 7.21–7.42(a.c., 5H); 7.52(d, J=8.5Hz, 2H) ($CDCl_3$) |
| 2 | H | H | H | H | H | C—$CH_3$ | N | Cl | CCl | 86–89° C. | 3196 (b.a., OH), 2951, 2924, 2824, 1406, 1247, 1146 762, 703 KBr | 1.59(m, J=5.3 J'=6.6, 2H); 1.70–1.32(a.c., 4H); 2.16 (d, t, J=13.0Hz J'=4.4Hz, 2H); 2.37(s, 3H); 2.41–2.55 (a.c., 5H); 2.79(d, J=11.3Hz, 2H); 3.88(t, J=7.5Hz, 2H); 7.27(t, J=7.2Hz, 1H); 7.36(t, J=7.6Hz, 2H); 7.51 (d, J=7.3Hz, 2H) ($CDCl_3$) |
| 3 | H | H | H | H | H | CH | N | CH═CH—CH═CH—C | | 122–123° C. | 3180 (b.a., OH), 2929, 2818, 1496, 1467, 1459, 1445, 1286, 1219, 1143, 769, 743, 707 KBr | 1.51 (quin, J=7.4Hz, 2H); 1.73(d, J=12.7Hz, 2H); 1.87 (quin, J=7.6Hz, 2H); 2.10(dt, J=12.9Hz J'=4.1Hz, 2H); 2.36–2.50(a.c., 4H); 2.70(d, J=11.2Hz, 2H); 3.25(b.a., 1H); 4.12(t, J=7.1Hz, 2H); 7.21–7.40(a.c., 6H); 7.51 (d, J=8.3Hz, 2H); 7.70–7.75(a.c., 2H) ($CDCl_3$) |
| 4 | H | H | H | H | H | CH | N | H | N | 123° C. | 3180 (b.a., OH), 2949, 2919, 2838, 1276, 1145, 1135, 1006, 770, 707, 676 KBr | 1.45(quin, J=7.5Hz, 2H); 1.69(d, J=12.9Hz, 2H); 1.85 quin, J=7.5Hz, 2H); 2.07(dt, J=13.0Hz J'=4.1Hz, 2H); 2.33–2.45(a.c., 4H); 2.69(d, J=11.2Hz, 2H); 2.93(b.a., 1H); 4.10(t, J=6.9Hz, 2H); 7.18(t, J=7Hz, 1H); 7.27 (t, J=7.8Hz, 2H); 7.46(d, J=8.3Hz, 2H); 7.80(s, 1H); 7.91(s, 1H) ($CDCl_3$) |
| 5 | H | H | Cl | H | H | N | CH | Cl | CH | 106° C. | 3145 (b.a., OH), 2947, 2918, 2834, 1318, 1147, 1083, 1112, 990, 817, 612 KBr | 1.47(quin, J=7.5Hz, 2H); 1.69(d, J=11.9Hz, 2H); 1.84 (quin, J=7.6Hz, 2H); 2.05(dt, J=13Hz, J'=4.4Hz, 2H); 2.34–2.50(a.c., 5H); 2.72(d, J=11.2Hz, 2H); 4.05 (t, J=7.0Hz, 2H); 7.29(AB system, J=8.6Hz, 2H); 7.36 (s, 2H); 7.42(AB system, J=8.6Hz, 2H) ($CDCl_3$) |
| 6 | H | H | Cl | H | H | C—$CH_3$ | N | Cl | CCl | oil | 3340 (b.a., OH), 2946, 2820, 1537, 1492, 1471, 1406, 1376, 1247, 1135, 1094, 1013, 828, 755 film | 1.54(m, 2H); 1.67–1.78(a.c., 4H); 2.06(dt, J=13Hz, J'=4.2Hz, 2H); 2.32(s, 3H); 2.38–2.45(a.c., 5H); 2.73 (d, J=11.2Hz, 2H); 3.86(t, J=7.3Hz, 2H); 7.28(AB system, J=8.6Hz, 2H); 7.43(AB system, J=8.6Hz, 2H) ($CDCl_3$) |
| 7 | H | $CF_3$ | H | H | H | N | CH | Cl | CH | oil | 3360 (b.a., OH), 2948, 2823, 1438, | 1.48(quin, J=7.6Hz, 2H); 1.71(d, J=12.5Hz, 2H); 1.85 (quin, J=7.6Hz, 2H); 2.06–2.21(a.c., 3H); 2.36–2.43 |

TABLE 1-continued

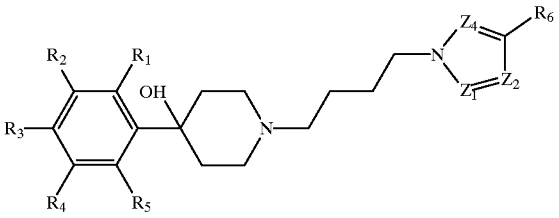

| Ex. | $R_1$ | $R_2$ | $R_3$ | $R_4$ | $R_5$ | $Z_1$ | $Z_2$ | $R_6$ | $Z_4$ | m.p. | IR $cm^{-1}$ | $^1$H-RMN (300 MHz), δ (solvent) |
|---|---|---|---|---|---|---|---|---|---|---|---|---|
| | | | | | | | | | | | 1378, 1330, 1212, 1165, 1124, 1047, 972, 804, 704 film | (a.c., 4H); 2.76(d, J=11.5Hz, 2H); 4.06(t, J=7.1Hz, 2H); 7.35(s, 2H); 7.43–7.51(a.c., 2H); 7.66 (d, J=7.5Hz, 1H); 7.79(s, 1H) ($CDCl_3$) |
| 8 | H | $CF_3$ | H | H | H | C—$CH_3$ | N | Cl | CCl | oil | 3340 (b.a., OH), 2948, 2823, 1408, 1330, 1165, 1126, 1075, 789, 763, 704 film | 1.57(quin, J=7.5Hz, 2H); 1.70–1.80(a.c., 4H); 2.15 (dt, J=12.9Hz J'=3.6Hz, 2H); 2.35(s, 3H); 2.40–2.52 (a.c., 4H); 2.80(d, J=11.7Hz, 2H); 3.88(t, J=7.0Hz, 2H); 7.42–7.57(a.c., 2H); 7.69(d, J=7.5Hz, 1H); 7.82 (s, 1H) ($CDCl_3$) |
| 9 | H | H | F | H | H | C—$CH_3$ | N | Cl | CCl | oil | 3330 (b.a., OH), 2946, 2818, 1509, 1406, 1247, 1222, 1160, 835 film | 1.58(m, 2H); 1.64–1.81(a.c., 4H); 2.14(dt, J=12.9Hz J'=3.6Hz 2H); 2.32(s, 3H); 2.43–2.60(a.c., 4H); 2.84 (d, J=11Hz, 2H); 3.87(t, J=7.1Hz, 2H); 4.18(b.a., 1H), 7.01(t, J=8.8Hz, 2H); 7.46(dd, J=8.8Hz J'=5.2Hz, 2H) ($CDCl_3$) |
| 10 | H | H | H | H | H | CH | CH | CH═CH—CH═CH—C | | 109–111° C. | 3190 (b.a., OH), 2956, 2823, 1461, 1446, 1319, 1303, 1218, 1142, 738, 703 KBr | 1.57(m, 2H); 1.73(d, J=14Hz, 2H); 1.80(b.a., 1H); 1.90(m, 2H); 2.13(dt, J=13Hz J'=4Hz, 2H); 2.32–2.46 (a.c., 4H); 2.76(d, J=11.3Hz, 2H); 4.16(t, J=7.1Hz, 2H); 6.50(d, J=3.1Hz, 1H); 7.05–7.14(a.c., 2H); 7.18–7.40(a.c., 5H); 7.50(d, J=7.8Hz, 2H); 7.00 (d, J=7.3Hz, 1H) ($CDCl_3$) |
| 11 | H | H | $CH_3$ | H | H | C—$CH_3$ | N | Cl | CCl | oil | 3360, (b.A., OH), 2946, 2818, 1535, 1471, 1406, 1376, 1247, 1134, 817, 755 | 1.53(m, 2H); 1.66–1.84(a.c., 4H); 2.09(dt, J=12.9Hz, J'=3.6Hz, 2H); 2.33(s, 3H); 2.36(s, 3H); 2.39–2.50 (a.c., 4H); 2.77(d, J=11.2Hz, 2H); 3.87(t, J=7.0Hz, 2H); 7.15(AB system, J=7.8Hz, 2H); 7.33(AB system, J=7.8Hz, 2H) ($CDCl_3$) |
| 12 | H | H | H | H | H | N | CH | H | CH | 89–91° C. | 3137 (b.A., OH) 2947, 2532, 1396, 1378, 1119, 1046, 756, 697 KBr | 1.51(quin, J=7.6Hz, 2H); 1.73(d, J=12.3Hz, 2H); 1.89 (quin, J=7.6Hz, 2H); 2.00–2.20(a.c., 3H); 2.35–2.45 (a.c., 4H); 2.76(d, J=10.2Hz, 2H); 4.13(t, J=7.1Hz, 2H); 6.21(s, 1H); 7.21(m, 1H); 7.30–7.37(a.c., 3H); 7.44–7.52(a.c., 3H) ($CDCl_3$) |
| 13 | H | H | H | H | H | N | CH | CH═CH—CH═CH—C | | 107–109° C. | 3311 (b.a., OH), 2953, 2803, 1465, 1375, 1133, 1117, 1043, 1017, 761, 744, 704 KBr | 1.53(m, 2H); 1.71(d, J=12.2Hz, 2H); 1.95(m, 2H); 2.10(m, 2H); 2.29(b.a., 1H); 2.35–2.47(a.c., 4H); 2.71(d, 2H); 4.39(t, J=7.1Hz, 2H); 7.13(t, 1H); 7.22–7.44(a.c., 5H); 7.50(d, J=8Hz, 2H); 7.71(d, J=8.3Hz, 1H); 7.95(s, 1H) ($CDCl_3$) |

TABLE 1-continued

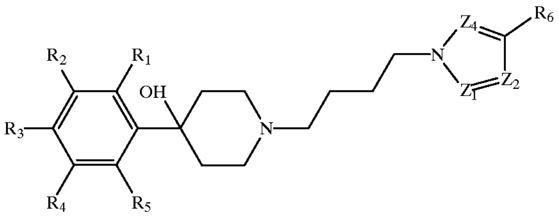

| Ex. | $R_1$ | $R_2$ | $R_3$ | $R_4$ | $R_5$ | $Z_1$ | $Z_2$ | $R_6$ | $Z_4$ | m.p. | IR $cm^{-1}$ | $^1$H-RMN (300 MHz), δ (solvent) |
|---|---|---|---|---|---|---|---|---|---|---|---|---|
| 14 | H | H | H | H | H | N | C—CH═CH—CH═CH | | CH | 120–122° C. | 3295 (b.a., OH) 2946, 2817, 1377, 1126, 786, 735, 700 KBr | 1.58(m, 2H); 1.73(d, J=13.5Hz, 2H); 1.90–2.20(a.c., 4H); 2.38–2.47(a.c., 4H); 2.75(d, J=10.5Hz, 2H); 4.42 (t, J=6.Hz, 2H); 7.06(t, J=7.5Hz, 1H); 7.22–7.37(a.c., 4H); 7.49(d, J=7.8Hz, 2H); 7.61–7.71(a.c., 2H); 7.90 (s, 1H) ($CDCl_3$) |
| 15 | H | H | $CH_3$ | H | H | N | CH | Cl | CH | 81–82° C. | 3122 (b.a., OH) 2936, 1475, 1434, 1378, 1319, 989, 973, 814 KBr | 1.51(quin, J=7.6Hz, 2H); 1.73(d, J=11.7Hz, 2H); 1.87 (quin, J=7.6Hz, 2H); 2.12(dt, J=12.8Hz J'=4.4Hz, 2H), 2.33(s, 3H); 2.35–2.48(a.c., 5H); 2.74(d, J=11.2Hz, 2H); 4.07(t, J=7.1Hz, 2H); 7.15(d, J=8Hz, 2H); 7.25–7.40(a.c., 4H) ($CDCl_3$) |
| 16 | H | H | $CH_3O$ | H | H | N | CH | Cl | CH | 122–123° C. | 3190 (b.a., OH) 2954, 2923, 2827, 1509, 1314, 1243, 1178, 971 KBr | 1.49(quin, J=7.6Hz, 2H); 1.72(d, J=11.8Hz, 2H); 1.84 (quin J=7.4Hz, 2H); 2.00–2.14(a.c.(dt+b.a.), 3H); 2.34–2.47(a.c., 4H); 2.72(d, J=11Hz, 2H); 3.77(s, 3H); 4.05(t, J=7.1Hz, 2H); 6.85(d, J=9Hz, 2H); 7.24–7.42(a.c., 4H) ($CDCl_3$) |
| 17 | H | H | H | H | H | CPh | N | H | CH | 108–110° C. | 3220 (b.a., OH) 2944, 2817, 1473, 1446, 1421, 1136, 1046, 787, 773, 761, 700 KBr | 1.45(quin, J=7.6Hz, 2H); 1.68–1.82(a.c., 4H); 2.08 (dt, J=13.0Hz J'=4.1Hz, 2H); 2.29–2.42(a.c., 4H); 2.5 (b.a., 1H); 2.67d, J=11.2Hz, 2H); 4.01 m(t, J=7.3Hz, 2H); 7.01(s, 1H); 7.08(s, 1H); 7.20–7.56(a.c., 10H) ($CDCl_3$) |
| 18 | H | H | $CH_3$ | H | H | CH | N | CH═CH—CH═CH—C | | oil | 3260 (b.a., OH) 2944, 2817, 1497, 1459, 1381, 1287, 1135, 1046, 817, 745 film | 1.58(quin, J=7.6Hz, 2H); 1.74(d, J=12Hz, 2H); 1.82 (b.a., 1H); 1.95(quin, J=7.6Hz, 2H); 2.11(dt, 2H); 2.33(s, 3H); 2.40–2.50(a.c., 4H); 2.74(d, J=11.5Hz, 2H); 4.20(t, J=7.1Hz, 2H); 7.15(d, J=8.3Hz, 2H); 7.22–7.35(a.c., 3H); 7.37–7.43(a.c., 2H); 7.79(m, 1H); 7.87(s, 1H) ($CDCl_3$) |
| 19 | H | H | H | H | H | CH | N | Ph | CPh | 138–139° C. | 3194(b.a., OH) 2939, 2806, 1509, 1446, 773, 766, 758, 696 KBr | 1.38(m, 2H); 1.56(m, 2H); 1.72(d, J=12.4Hz, 2H); 2.09(dt, 2H); 2.25(t, J=7.4Hz, 2H); 2.39(m, 2H); 2.66 (m, 2H); 3.10(b.a., 1H); 3.78(t, J=7.2Hz, 2H); 7.10–7.52(a.c., 16H); |
| 20 | CH═CH—CH═CH | | H | H | H | N | CH | Cl | CH | oil | 3357 (b.a., OH), 2946, 2833, 1434, 1379, 1315, 1140, 1123, 972, 781, 613 KBr | 1.44(quin, J=7.3Hz, 2H); 1.77(quin, J=7.5Hz, 2H); 2.15–2.30(a.c., 5H); 2.34(t, J=7.5Hz, 2H); 2.57(m, 2H); 2.73(d, J=11.3Hz, 2H); 3.99(t, J=7.1Hz, 2H); 7.26–7.46 (a.c., 6H); 7.73(d, J=8.1Hz, 1H); 7.82(m, 1H); 8.91 (m, 1H) ($CDCl_3$) |

TABLE 1-continued

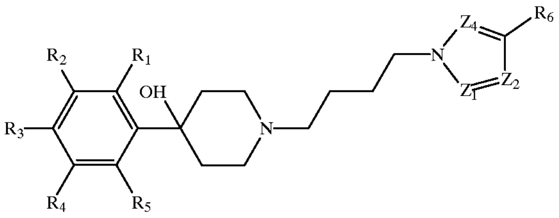

| Ex. | $R_1$ | $R_2$ | $R_3$ | $R_4$ | $R_5$ | $Z_1$ | $Z_2$ | $R_6$ | $Z_4$ | m.p. | IR $cm^{-1}$ | $^1$H-RMN (300 MHz), δ (solvent) |
|---|---|---|---|---|---|---|---|---|---|---|---|---|
| 21 | H | CH═CH—CH═CH | | H | H | N | CH | Cl | CH | 142–143° C. | 3131 (b.a., OH), 2950, 2820, 1377, 1311, 971, 829, 761, 613 KBr | 1.55(quin, J=7.5Hz, 2H); 1.70–1.97(a.c., 5H); 2.29 (dt, J=12.7Hz, J'=4.1Hz, 2H); 2.41–2.55(a.c., 4H); 2.83 (d, J=11.7Hz, 2H); 4.11(t, J=7.0Hz, 2H); 7.39–7.50 (a.c., 4H); 7.64(dd, J=9.1Hz, J'=1.5Hz, 1H); 7.81–7.85 (a.c., 3H); 7.95(s, 1H) ($CDCl_3$) |
| 22 | H | H | H | H | H | N | CH | $C_6$HCl | CH | 137–140° C. | 3347, 2944, 2810, 1562, 1492, 1376, 1127, 1094, 1002, 952, 828, 760, 699 KBr | 1.56(m, 2H); 1.74(m, 2H); 1.80(b.a., 1H); 1.94(m, 2H); 2.40(dt, J=13.1Hz, J'=4.0Hz, 2H); 2.40–2.50(a.c., 4H); 2.77(m, 2H); 4.15(t, J=7.0Hz, 2H); 7.25–7.40 (a.c., 7H); 7.50(d, J=8.3Hz, 2H); 7.61(s, 1H); 7.72 (s, 1H) ($CDCl_3$) |
| 23 | H | H | F | H | H | CH | N | CH═CH—CH═CH—C | | 120–122° C. | 3230, 2947, 2915, 1504, 1219, 1135, 835, 746 KBr | 1.58(m, 2H); 1.70(m, 2H); 1.93(m, 2H); 2.12(m, 2H); 2.40–2.55(a.c., 4H); 2.76(m, 2H); 4.19(t, J=7.0Hz, 2H); 7.02(m, 2H); 7.26(m, 2H); 7.30–7.50(a.c., 3H); 7.74(m, 1H); 7.83(s, 1H) ($CDCl_3$) |
| 24 | H | $CF_3$ | H | H | H | N | CH | Cl | CH | HCl 147–148° C. | 3259, 2465, 2420, 2365, 1328, 1108, 1073 KBr | 1.62–1.84(a.c., 6H); 2.53(m, 2H); 3.09–3.40(a.c., 6H); 4.12(t, J=6.8Hz, 2H); 5.76(s, 1H); 7.51(s, 1H); 7.52–7.82(a.c., 4H); 8.02(s, 1H); 10.96(b.a., 1H) (DMSO-$d_6$) |
| 25 | H | H | F | H | H | N | CH | CH═CH—CH═CH—C | | 136–137° C. | 3303, 2951, 2805, 1506, 1464, 1376, 1218, 1162, 1118, 832, 741 KBr | 1.54(m, 2H); 1.60–1.80(a.c., 3H); 1.97(m, 2H); 2.06 (dt, J=13.0Hz, J'=4.3Hz, 2H); 2.30–2.43(a.c. 4H, 2.72 (m, 2H); 4.40(t, J=7.0Hz, 2H); 6.99(t, J=8.8Hz, 2H), 7.12(m, 1H); 7.32–7.47(a.c., 4H); 7.71(d, J=8.1Hz, 1H); 7.96(s, 1H) ($CDCl_3$-$CD_3OD$ [1:1]) |
| 26 | H | H | F | H | H | N | C—CH═CH—CH═CH | | CH | 148–150° C. | 3325, 2950, 2923, 2812, 1509, 1377, 1218, 1131, 834, 758 KBr | 1.57(m, 2H); 1.70–1.77(a.c., 3H); 1.98–2.19(a.c., 4H); 2.35–2.49(a.c., 4H); 2.77(d, J=11.2Hz, 2H); 4.45 (t, J=7.0Hz, 2H); 6.98–7.15(a.c., 3H); 7.25–7.49(a.c., 3H); 7.63(d, J=8.3Hz, 1H); 7.69(d, J=7.8Hz, 1H); 7.91 (s, 1H) ($CDCl_3$-$CD_3OD$ [1:1]) |
| 27 | H | H | F | H | N | N | C—CH═CH—CH═CH | | N | 109–110° C. | 3400, 2931, 2812, 1509, 1229, 1101, 831, 745 KBr | 1.47–1.80(a.c., 4H); 1.90–2.25(a.c., 5H); 2.25–2.55 (a.c., 4H); 2.70(m, 2H); 4.78(t, J=6.9Hz, 2H); 7.01 (t, J=8.7Hz, 2H); 7.26–7.54(a.c., 4H); 7.85(dd, J=6.7Hz, J'=3.0Hz, 2H) ($CDCl_3$-$CD_3OD$ [1:1]) |
| 28 | H | H | F | H | H | N | N | CH═CH—CH═CH—C | | 102–103° C. | 3430, 2952, 2925, 1508, 1223, 1140, | 1.45–1.80(a.c., 4H); 1.85–2.25(a.c., 5H); 2.25–2.55 (a.c., 4H); 2.77(m, 2H); 4.69(t, J=6.9Hz, 2H); 7.01 |

TABLE 1-continued
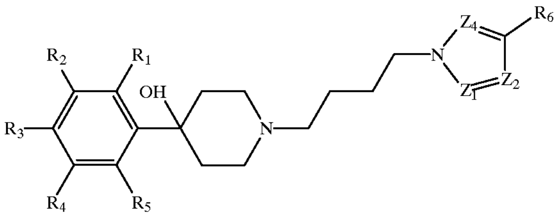
| Ex. | $R_1$ | $R_2$ | $R_3$ | $R_4$ | $R_5$ | $Z_1$ | $Z_2$ | $R_6$ | $Z_4$ | m.p. | IR $cm^{-1}$ | $^1H$-RMN (300 MHz), δ (solvent) |
|---|---|---|---|---|---|---|---|---|---|---|---|---|
| | | | | | | | | | | | 833, 744 KBr | (t, J=8.7Hz, 2H); 7.26–7.53(a.c., 5H); 8.06(d, J=7.3Hz, 1H) ($CDCl_3$-$CD_3OD$ [1:1]) |
| 29 | H | H | F | H | H | CH | N | H | N | oil | 3350 (b.a., OH), 2947, 2818, 1509, 1222, 1138, 836, 681 film | 1.55(m, 2H); 1.74(d, J=12.6Hz, 2H); 1.94(m, 2H); 2.13(m, 2H); 2.40–2.55(a.c.; 4H); 2.79(m, 2H); 4.20 (t, J=6.9Hz, 2H); 7.02(t, J=8.4Hz, 2H); 7.46(m, 2H); 7.91(s, 1H); 8.04(s, 1H) ($CDCl_3$) |
| 30 | H | H | Cl | H | H | CH | N | H | N | 89–91° C. | 3119 (b.a., OH), 2956, 2829, 1509, 1379, 1277, 1145, 1007, 824, 685 KBr | 1.46(m, 2H); 1.71(m, 2H); 1.90(quin, J=7.4Hz, 2H); 2.05(m, 2H); 2.33–2.50(a.c., 4H); 2.54(b.a., 1H); 2.72 (m, 2H); 4.16(t, J=7.1Hz, 2H); 7.28(m, 2H); 7.42(m, 2H); 7.86(s, 1H); 7.99(s, 1H) ($CDCl_3$) |

TABLE 2

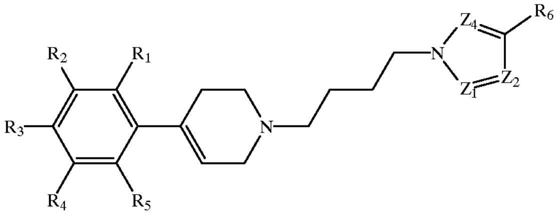

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| 1a | H | H | H | H | H | N | CH | Cl | CH | 62–64° C. | 3113, 2920, 2745, 1375, 1325, 1138, 965, 837, 742, 688 | 1.56(quin, J=7.6Hz, 2H); 1.91(quin, J=7.6Hz, 2H); 2.47(t, J=7.4Hz, 2H); 2.58(m, 2H); 2.65 (t, J=5.6Hz, 2H); 3.14(m, 2H); 4.11(t, J=7.1Hz, 2H); 6.06(m, 1H); 7.23–7.42(a.c., 7H) ($CDCl_3$) |
| 2a | H | H | H | H | H | CH | N | CH=CH—CH=CH—C | | 66–69° C. | 2933, 1495, 745, 694, 665 film | 1.55(quin, J=7.6Hz, 2H); 1.92(quin, J=7.6Hz, 2H); 2.43(t, J=7.3Hz, 2H); 2.52(m, 2H); 2.61 (t, J=5.6Hz, 2H); 3.07(m, 2H); 4.14(t, J=7.1Hz, 2H); 6.02(m, 1H); 7.20–7.40(a.c., 8H); 7.80(m, 1H); 7.86(s, 1H) ($CDCl_3$) |
| 3a | H | H | H | H | H | CH | N | H | N | 63–64° C. | 2942, 1438, 1381, 1271, 1142, 1006, 753, 697, 681, KBr | 1.56(m, 2H); 1.95(m, 2H); 2.47(t, J=7.1Hz, 2H); 2.56(m, 2H); 2.66(t, J=5.3Hz, 2H); 3.11 (m, 2H); 4.19(t, J=7.0Hz, 2H); 6.05(s, 1H); 7.21 (m, 1H); 7.30(t, J=7.6Hz, 2H); 7.36(d, J=7.8Hz, 2H); 7.94(s, 1H); 8.06(s. 1H) ($CDCl_3$) |
| 4a | H | H | Cl | H | H | N | CH | Cl | CH | 103–104° C. | 2939, 1493, 1436, 1381, 1306, 1122, 1097, 973, 843, 824, 730 KBr | 1.54(m, 2H); 1.90(m, 2H); 2.45(t, J=7.4Hz, 2H); 2.51(m, 2H); 2.65(t, J=5.6Hz, 2H); 3.10 (m, 2H); 4.10(t, J=7.0Hz, 2H); 6.03(m, 1H); 7.26(AB system, J=8.6Hz, 2H); 7.29(AB system, J=8.6Hz, 2H); 7.37(s, 1H); 7.41(s, 1H) ($CDCl_3$) |
| 5a | H | H | Cl | H | H | C—$CH_3$ | N | Cl | CCl | 119–120° C. | 2922, 1531, 1494, 1469, 1403, 1380, 1366, 1245, 1094, 1010 KBr | 1.59(m, 2H); 1.76(m, 2H); 2.36(s, 3H); 2.42–2.53(a.c., 4H); 2.67(t, J=5.3Hz, 2H); 3.12(m, 2H); 3.88(t, J=7.4Hz, 2H); 6.04(m, 1H); 7.27 (AB system, J=9.1Hz, 2H); 7.30(AB system, J=9.1Hz, 2H) ($CDCl_3$) |
| 6a | H | $CF_3$ | H | H | H | N | CH | Cl | CH | oil | 2944, 1434, 1375, 1331, 1247, 1165, 1126, 1076, 972, 800, 698 film | 1.53, (quin, J=7.5Hz, 2H); 1.89(quin, J=7.7Hz, 2H); 2.45(t, J=7.3Hz, 2H); 2.54(m, 2H); 2.66 (t, J=5.5Hz, 2H); 3.10(m, 2H); 4.08(t, J=7.1Hz, 2H); 6.10(m, 1H); 7.35–7.56(a.c., 5H); 7.59(s, 1H) ($CDCl_3$) |
| 7a | H | $CF_3$ | H | H | H | C—$CH_3$ | N | Cl | CCl | oil | 2931, 2815, 1533, 1405, 1331, 1246, 1165, 1125, 1076, 797, 699 film | 1.62(quin, J=6.6Hz, 2H); 1.77(quin, J=7.6Hz, 2H); 2.37(s, 3H); 2.51(t, J=7.2Hz, 2H); 2.60(m, 2H); 2.71(t, J=5.6Hz, 2H); 3.17(m, 2H); 3.89 (t, J=7.3Hz, 2H); 6.14(m, 1H); 7.40–7.50(a.c., 2H); 7.55(d, J=7.5Hz, 1H); 7.62(s, 1H) ($CDCl_3$) |
| 8a | H | H | F | H | H | N | CH | Cl | CH | 86–87° C. | 2936, 1512, 1378, 1326, 1229, 988, | 1.60(quin, J=7.5Hz, 2H); 1.91(quin, J=7.5Hz, 2H); 2.50–2.82(a.c., 4H); 2.76(t, J=5.6Hz, 2H); |

TABLE 2-continued

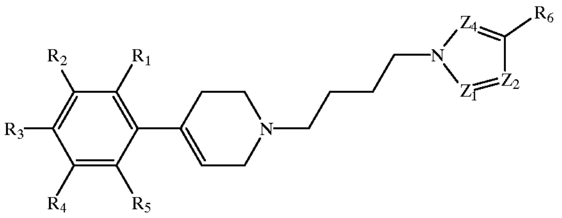

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| | | | | | | | | | | | 967 KBr | 3.19(m, 2H); 4.11(t, J=6.9Hz, 2H); 5.97(s, 1H); 6.99(t, J=8.8Hz, 2H); 7.32(dd, J=8.8Hz J'=5.4Hz, 2H); 7.38(s, 1H); 7.40(s, 1H) ($CDCl_3$) |
| 9a | H | H | F | H | H | C—$CH_3$ | N | Cl | CCl | 79–82° C. | 2934, 1531, 1512, 1408, 1247, 1225, 1167, 818 KBr | 1.74(m, 4H); 2.35(s, 3H); 2.60–2.72(a.c., 4H); 2.90(m. 2H); 3.33(m, 2H); 3.88(m, 2H); 5.95(s, 1H); 6.99(t, J=8.6Hz, 2H); 7.31(a.c., 2H) ($CDCl_3$) |
| 10a | H | H | H | H | H | C—$CH_3$ | N | Cl | CCl | oil | 2929, 1533, 1405, 1246, 748 film | 1.59(m, 2H); 1.76(m, 2H); 2.37(s, 3H); 2.49 (t, J=7.3Hz, 2H); 2.58(m, 2H); 2.69(t, J=5.4Hz, 2H); 3.14(m, 2H); 3.89(t, J=7.4Hz, 2H); 6.06 (m, 1H); 7.22–7.40(a.c., 5H) ($CDCl_3$) |
| 11a | H | H | H | H | H | C—$CH_3$ | N | Cl | CCl | .HCl 203–204° C. | 2930, 2576, 1407, 1376, 1245, 750, KBr | 1.69(m, 2H); 1.81(m, 2H); 2.35(s, 3H); 2.71 (d, J=7.2Hz, 1H); 2.91(m, 1H); 3.17(a.c., 3H); 3.56(m, 1H); 3.75(m, 1H); 3.90–3.97(a.c., 3H); 6.17(s, 1H); 7.25–7.40(a.c., 3H); 7.47 (d, J=7.6Hz, 2H); 11.30(b.a., 1H) (DMSO-$d_6$) |
| 12a | H | H | H | H | H | C—$CH_3$ | N | Cl | CCl | .2HCl 192–194° C. | 3569, 2941, 2692, 2556, 1601, 1446, 769, 753, 698 KBr | 1.67(m, 2H); 1.79(m, 2H); 2.36(s, 3H); 2.69 (d, J=18.0Hz, 1H); 2.88(m, 1H); 3.15(a.c., 3H); 3.54(m, 1H); 3.72(m, 1H); 3.85–398(a.c., 3H); 6.15(s, 1H); 7.22–7.38(a.c., 3H); 7.45 (d, J=7.3Hz, 2H); 9.93(b.a., 1H); 11.36(b.a., 1H) (DMSO-$d_6$) |
| 13a | H | H | F | H | H | CH | CH | CH═CH—CH═CH—C | | oil | 2937, 1510, 1464, 1230, 1161, 816, 742 film | 1.61(quin, J=7.7Hz, 2H); 1.93(quin, J=7.6Hz, 2H); 2.42–2.58(a.c., 4H); 2.66(t, J=5.6Hz, 2H); 3.11(m, 2H); 4.17(t, J=7.0Hz, 2H); 5.98(m, 1H); 6.51(d, J=3.9Hz, 1H); 6.95–7.39(a.c., 8H); 7.65(d, J=7.8Hz, 1H) ($CDCl_3$) |
| 14a | H | H | H | H | H | CH | CH | CH═CH—CH═CH—C | | oil | 2938, 1510, 1485, 1463, 1446, 1376, 1336, 1315, 763, 740, 695 film | 1.63(quin, J=7.4Hz, 2H); 1.94(quin, J=7.4Hz, 2H); 2.49(t, J=7.6Hz, 2H); 2.60(m, 2H); 2.69 (t, J=5.3Hz, 2H); 3.14(m, 2H); 4.19(t, J=7.1Hz, 2H); 6.08(m, 1H); 6.53(m, 1H); 7.08–7.44(a.c., 9H); 7.67(d, J=8.1Hz, 1H) ($CDCl_3$) |
| 15a | H | H | $CH_3$ | H | H | C—$CH_3$ | N | Cl | CCl | 87–88° C. | 2939, 2916, 1529, 1404, 1378, 1243, 1166, 1131, 1016 film | 1.59(m, 2H); 1.75(m, 2H); 2.32(s, 3H); 2.36(s, 3H); 2.47(t, J=7.2Hz, 2H); 2.54(m, 2H); 2.67 (t, J=5.2Hz, 2H); 3.11(m, 2H); 3.87(t, J=7.3Hz, 2H); 6.01(s, 1H); 7.11(AB system, J=8.1Hz, 2H); 7.27(AB system, J=8.1Hz, 2H) ($CDCl_3$) |

TABLE 2-continued

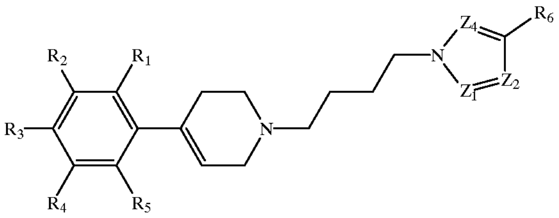

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| 16a | H | H | H | H | H | N | CH | H | CH | 36–38° C. | 2941, 1396, 748, 695 film | 1.54(quin, J=7.6Hz, 2H); 1.91(quin, J=7.6Hz, 2H); 2.45(t, J=7.6Hz, 2H); 2.55(m, 2H); 2.65 (t, J=5.6Hz, 2H); 3.11(m, 2H); 4.14(t, J=7.1Hz, 2H); 6.03(m, 1H); 6.21(m, 1H); 7.20–7.39(a.c., 6H); 7.49(m, 1H) ($CDCl_3$) |
| 17a | H | H | H | H | H | N | CH | CH═CH—CH═CH—C | | 50–52° C. | 2942, 1465, 1158, 832, 740, 691 KBr | 1.61(quin, 2H); 2.00(quin, J=7.5Hz, 2H); 2.43–2.58(a.c., 4H); 2.68(m, 2H); 3.14(s, 2H); 4.43 (t, J=6.6Hz, 2H); 6.02(s, 1H); 7.13(t, J=7.3Hz, 1H); 7.20–7.51(a.c., 7H); 7.73(d, J=7.9Hz, 1H); 7.99(s, 1H) ($CDCl_3$) |
| 18a | H | H | H | H | H | N | C—CH═CH—CH═CH | | CH | 73–75° C. | 3049, 2940, 2778, 1467, 1371, 1158, 1143, 1131, 757, 742, 692 KBr | 1.60(quin, J=7.6Hz, 2H); 2.09(quin, J=7.4Hz, 2H); 2.48(t, J=7.4Hz, 2H); 2.55(m, 2H); 2.66 (t, J=5.6Hz, 2H); 3.11(d, J=2.9Hz, 2H); 4.45 (t, J=7.1Hz, 2H); 6.03(s, 1H); 7.07(t, J=7.5Hz, 1H); 7.20–7.39(a.c., 6H); 7.63(d, J=4.3Hz, 1H); 7.70(d, J=8Hz, 1H); 7.91(s, 1H) ($CDCl_3$) |
| 19a | H | H | $CH_3$ | H | H | N | CH | Cl | CH | 72–73° C. | 3115, 2938, 2740, 1376, 1328, 1137, 986, 966, 844, 824, 797 KBr | 1.55(quin, 2H); 1.90(quin, J=7.5Hz, 2H); 2.33 (s, 3H); 2.46(t, J=7.5Hz, 2H); 2.55(m, 2H); 2.66 (t, J=6.4Hz, 2H); 3.11(m, 2H); 4.10(t, J=7.0Hz, 2H); 6.01(s, 1H); 7.12(AB system, J=8Hz, 2H); 7.27(AB system, J=8Hz, 2H); 7.37(s, 1H); 7.41 (s, 1H) ($CDCl_3$) |
| 20a | H | H | $CH_3O$ | H | H | N | CH | Cl | CH | 104–105° C. | 2923, 1533, 1405, 1379, 1246, 749 KBr | 1.54(quin, 2H); 1.89(quin, J=7.6Hz, 2H); 2.44 (t, J=7.4Hz, 2H); 2.52(m, 2H); 2.65(t, J=5.3Hz, 2H); 3.10(m, 2H); 3.78(s, 3H); 4.09(t, J=7.0Hz, 2H); 5.95(s, 1H); 6.84(AB system, J=8.5Hz, 2H); 7.31(AB system, J=8.5Hz, 2H); 7.36(s, 1H); 7.40(s, 1H) ($CDCl_3$) |
| 21a | H | H | H | H | H | N | CH | Cl | CH | oil | 2948, 223, 2811, 2774, 1446, 1382, 1316, 971, 748, 695 film | 2.08(quin, J=7.0Hz, 2H); 2.42(t, J=7.0Hz, 2H); 2.58(m, 2H); 2.67(t, J=5.6Hz, 2H); 3.13(m, 2H); 4.17(t, J=6.9Hz, 2H); 6.07(m, 1H); 7.23–7.45(a.c., 7H) ($CDCl_3$) |
| 22a | H | H | H | H | H | $CCH_3$ | N | Cl | CCl | oil | 2923, 1533, 1405, 1379, 1246, 749 film | 1.95(quin, J=7.2Hz, 2H); 2.39(s, 3H); 2.46 (t, J=7.0Hz, 2H); 2.58(m, 2H); 2.69(t, J=4.9Hz, 2H); 3.13(m, 2H); 3.96(t, J=7.3Hz, 2H); 6.07 (m, 1H); 7.20–7.41(a.c., 5H) ($CDCl_3$) |

TABLE 2-continued

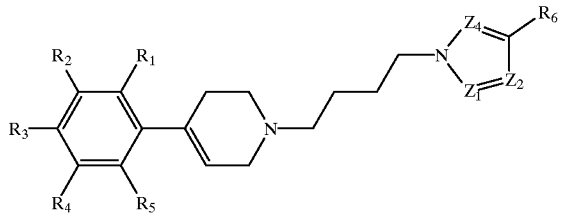

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1H$-RMN (300 MHz), δ (solvent) |
|---|---|---|---|---|---|---|---|---|---|---|---|---|
| 23a | H | H | H | H | H | CPh | N | H | CH | oil | 2940, 1496, 1474, 1445, 1379, 1275, 774, 698 film | 1.51(m, 2H); 1.81(m, 2H); 2.40(t, J=7.4Hz, 2H); 2.56(m, 2H); 2.63(t, J=4.9Hz, 2H); 3.09 (m, 2H); 4.04(t, J=7.2Hz, 2H); 6.03(m, 1H); 7.03(m, 1H); 7.13(m, 1H); 7.22–7.48(a.c., 8H); 7.58(m, 2H) ($CDCl_3$) |
| 24a | H | H | $CH_3$ | H | H | CH | N | CH=CH—CH=CH—C | | 90–91° C. | 2939, 2915, 1500, 1461, 1377, 1365, 750 KBr | 1.59(m, 2H); 1.95(m, 2H); 2.32(s, 3H); 2.46 (t, J=7.3Hz, 2H); 2.53(m, 2H); 2.63(t, J=5.5Hz, 2H); 3.08(m, 2H); 4.20(t, J=6.95Hz, 2H); 6.00 (s, 1H); 7.11(d, J=7.8Hz, 2H); 7.27(a.c., 4H); 7.40(m, 1H); 7.80(m, 1H); 7.8(s, 1H) ($CDCl_3$) |
| 25a | H | H | H | H | H | CH | N | Ph | CPh | 100–101° C. | 3130, 2939, 2770, 1600, 1506, 1443, 1259, 954, 780, 774, 750, 696, 649 KBr | 1.46(quin, J=7.5Hz, 2H); 1.65(quin, J=7.6Hz, 2H); 2.33(t, J=7.3Hz, 2H); 2.53(m, 2H); 2.60 (m, 2H); 3.05(m, 2H); 3.84(t, J=7.2Hz, 2H); 6.02(m, 1H); 7.05–7.50(a.c., 15H); 7.61(s, 1H) ($CDCl_3$) |
| 26a | CH=CH—CH=CH | | H | H | H | N | CH | Cl | CH | oil | 3057, 3043, 2942, 2806, 2768, 1378, 1365, 971, 801, 778 film | 1.61(quin, J=7.5Hz, 2H); 1.95(quin, J=7.6Hz, 2H); 2.51–2.57a.c., 4H); 2.76(t, J=5.6Hz, 2H); 3.20(m, 2H); 4.14(t, J=7.1Hz, 2H); 5.74(m, 1H); 7.26–7.50(a.c., 6H); 7.75(d, J=8Hz, 1H); 7.84(m, 1H); 8.02(m, 1H); ($CDCl_3$) |
| 27a | H | CH=CH—CH=CH | | H | H | N | CH | Cl | CH | 95–96° C. | 3111, 2920, 2806, 1374, 1326, 966, 826, 749, 612, KBr | 1.57(m, 2H); 1.92(m, 2H); 2.48(m, 2H); 2.71 (a.c, 4H); 3.18(m, 2H); 4.11(m, 2H); 6.22(m, 1H); 7.38–7.50(a.c., 4H); 7.61(m, 1H); 7.75–7.84(a.c., 4H) ($CDCl_3$) |
| 28a | H | H | F | H | H | CH | N | CH=CH—CH=CH—C | | 135–136° C. | 3050, 2920, 2780, 2760, 1510, 1492, 1459, 1224, 1202, 1161, 771, 751 KBr | 2.54(m, 2H); 2.74t, J=5.6Hz, 2H); 2.92(t, J=6.7Hz, 2H); 3.24(m, 2H); 4.35(t, J=6.7Hz, 2H); 5.98(m, 1H); 7.00(t, J=8.7Hz); 7.26–7.40(a.c., 4H); 7.42(m, 1H); 7.81(m, 1H); 8.01(s, 1H) ($CDCl_3$) |
| 29a | H | H | H | H | H | CH | N | CH=CH—CH=CH—C | | HCl 177–178° C. | 2940, 2488, 1500, 1420, 1390, 742 KBr | 1.70–1.90(a.c., 4H); 2.78(m, 2H); 3.17(m, 2H); 3.20–3.50(b.a., 2H); 3.79(m, 2H); 4.30(t, J=6.6Hz, 2H); 6.15(s, 1H); 7.17–7.40(a.c., 5H); 7.45(d, J=7.3Hz, 2H); 7.65(m, 2H); 8.35(s, 1H) (DMSO-$d_6$) |

TABLE 2-continued

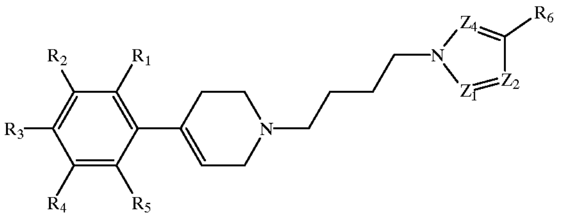

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| 30a | H | H | F | H | H | CH | N | CH═CH—CH═CH—C | | 106–108° C. | 2942, 1512, 1498, 1460, 1376, 1221, 756 KBr | 1.59(quin, J=7.5Hz, 2H); 1.96(quin, J=7.5Hz, 2H); 2.40–2.50(a.c., 4H); 2.63(t, J=5.5Hz, 2H); 3.09(m, 2H); 4.21 (t, J=7.1Hz, 2H); 5.97(m, 1H); 6.98(t, J=8.1Hz, 2H); 7.20–7.35(a.c., 4H); 7.40(m, 1H); 7.80(m, 1H); 7.89(s, 1H) ($CDCl_3$) |
| 31a | H | H | F | H | H | CH | N | CH═CH—CH═CH—C | | HCl | 2930, 1600, 1510, 1275 KBr | 1.70–2.00(a.c., 4H); 2.78(m, 2H); 3.20(m, 2H); 3.20–3.60(b.a., 2H); 3.81(m, 2H); 4.38(t, J=6.6Hz, 2H); 6.13 (s, 1H); 7.19(t, J=8.7Hz, 2H); 7.33(m, 2H); 7.49(m, 2H); 7.71(d, J=7.8Hz, 1H); 7.77(d, J=7.6Hz, 1H); 8.79 (s, 1H); 11.20(b.a., 1H) (DMSO-$d_6$) |
| 32a | H | $CF_3$ | H | H | H | $CCH_3$ | N | Cl | CCl | HCl 205–206° C. | 2930, 2490, 1330, 1243, 1164, 1119, | 1.67(m, 2H); 1.79(m, 2H); 2.33(s, 3H); 2.79(m, 1H); 2.91(m, 1H); 3.10–3.20(a.c., 3H); 3.55(m, 1H); 3.77 (m, 1H); 3.91–4.00(a.c., 3H); 6.33(s, 1H); 7.58–7.80 (a.c., 4H); 11.32(b.a., 1H) (DMSO-$d_6$) |
| 33a | H | H | F | H | H | N | CH | Cl | CH | HCl 191–192° C. | 2543, 1512, 1232, 967, 807 KBr | 1.71–1.85(a.c., 4H); 2.68(m, 1H); 2.86(m, 1H); 3.10–3.20(a.c., 3H); 3.55(m, 1H); 3.72(m, 1H); 3.90(m, 1H); 4.12(t, J=6.5Hz, 2H); 6.14(s, 1H); 7.20(t, J=8.7Hz, 2H); 7.40–7.55(a.c., 3H); 8.06(s, 1H); 11.20(b.a., 1H) (DMSO-$d_6$) |
| 34a | H | H | H | H | H | N | CH | CH═CH—CH═CH—C | | HCl 193–194° C. | 2931, 2566, 742 KBr | 1.80(m, 2H); 1.91(m, 2H); 2.67(m, 1H); 2.88(m, 1H); 3.10–3.20(a.c., 3H); 3.52(m, 1H); 3.71(m, 1H); 3.90 (m, 1H); 4.46(t, J=6.7Hz, 2H); 6.15(s, 1H); 7.14 (t, J=7.5Hz, 1H); 7.25–7.41(a.c., 4H); 7.46(d, J=8.6Hz, 2H); 7.71(d, J=8.6Hz, 1H); 7.75(d, J=8.3Hz, 1H); 8.08 (s, 1H); 11.18(b.a., 1H) (DMSO-$d_6$) |
| 35a | H | H | F | H | H | $CCH_3$ | N | Cl | CCl | HCl 160–161° C. | 2930, 2590, 1512, 1409, 1241, 827 KBr | 1.67(m, 2H); 1.79(m, 2H); 2.33(s, 3H); 2.67(m, 1H); 2.90(m, 1H); 3.10–3.25(a.c., 3H); 3.54(m, 1H); 3.72 (m, 1H); 3.85–3.98(a.c., 3H); 6.13(s, 1H); 7.19(m, 2H); 7.50(m, 2H); 11.28(b.a., 1H) (DMSO-$d_6$) |
| 36a | H | H | H | H | H | N | CH | 4-ClPh | CH | HCl 198–199° C. | 2472, 1560, 1450, 1095, 955, 810, 745 KBr | 1.77(m, 2H); 1.87(m, 2H); 2.70(m, 1H); 2.86(m, 1H); 3.16(a.c., 3H); 3.55(m, 1H); 3.73(m, 1H); 3.90(m, 1H); 4.17(t, J=6.6Hz, 2H); 6.15(m, 1H); 7.25–7.47(a.c., 7H); 7.59(m, 2H); 7.90(s, 1H); 8.27(s, 1H); 10.91 (b.a., 1H) (DMSO-$d_6$) |
| 37a | H | H | H | H | H | N | CH | 4-ClPh | CH | 126–127° C. | 2935, 1570, 1493, 1455, 1379, | 1.60(m, 2H); 1.97(m, 2H); 2.48(t, J=7.3Hz, 2h); 2.56 (m, 2H); 2.67(t, J=5.1Hz, 2H); 3.13(m, 2H); 4.18 (t, J=7.1Hz, 2H); 6.05(m, 1H); 7.23–7.40(a.c., 9H); 7.61 |

TABLE 2-continued

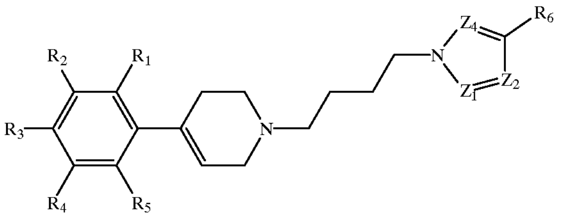

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| | | | | | | | | | | | 1091, 953, 815, 746 KBr | (s, 1H); 7.74(s, 1H) ($CDCl_3$) |
| 38a | H | H | F | H | H | CH | N | H | N | HCl 166–168° C. | 3450, 2429, 2707, 2593, 1512, 1437, 1230, 816, 626 KBr | 1.74(m, 2H); 1.86(m, 2H); 2.68(m, 1H); 2.84(m, 1H); 3.16(a.c., 3H); 3.53(m, 1H); 3.70(m, 1H); 3.91(m, 1H); 4.27(t, J=6.7Hz, 2H); 6.12(s, 1H); 7.19(t, J=8.9Hz, 2H); 7.50(dd, J=8.9Hz, J'=5.5Hz, 2H); 8.23(s, 1H); 8.93 (s, 1H); 11.02(b.a., 1H) (DMSO-$d_6$) |
| 39a | H | H | F | H | H | CH | N | H | N | oil | 2944, 2808, 2773, 1602, 1510, 1273, 1227, 1161, 1140, 846, 824, 681 film | 1.60(m, 2H); 1.97(m, 2H); 2.40–2.70(a.c., 6H); 3.12 (m, 2H); 4.22(t, J=6.9Hz, 2H); 5.99(m, 1H); 6.98(m, 2H); 7.35(m, 2H); 7.95(s, 1H); 8.07*s. 1H) ($CDCl_3$) |
| 40a | H | H | F | H | H | $CCH_3$ | N | CH═CH—CH═CH—C | | oil | 2932, 1512, 1456, 1404, 1231, 744 film | 1.63(m, 2H); 1.88(m, 2H); 2.42–2.55(a.c., 4H); 2.61 (s. 3H); 2.65(t, J=5.5Hz, 2H); 3.09(m, 2H); 4.14 (t, J=7.3Hz, 2H); 5.97(m, 1H); 6.99(m, 2H); 7.19–7.35 (a.c., 5H); 7.68(m, 1H) ($CDCl_3$) |
| 41a | H | H | F | H | H | N | CH | CH═CH—CH═CH—C | | oil | 2932, 2805, 1511, 1465, 1230, 1160, 825, 752, 741 film | 1.57(m, 2H); 1.99(m, 2H); 2.42–2.50(a.c., 4H); 2.62 (t, J=5.6Hz, 2H); 3.06(m, 2H); 4.42(t, J=6.9Hz, 2H); 5.95(m, 1H); 6.97(t, J=8.8Hz, 2H); 7.12(m, 1H); 7.25–7.41(a.c., 4H); 7.71(d, J=8Hz, 1h); 7.99(s, 1H) ($CDCl_3$) |
| 42a | H | H | F | H | H | N | C—CH═CH—CH═CH | | CH | 102–103° C. | 2941, 1510, 1374, 1226, 1162, 806, 759, 741 KBr | 1.59(quin, J=7.0Hz, 2H); 2.09(quin., J=7.5Hz, 2H); 2.40–2.50(a.c., 4H); 2.64(t, J=6.2Hz, 2H); 3.10(m, 2H); 4.45(t, J=7.1Hz, 2H); 5.96(m, 1H); 6.98(t, J=8.8Hz, 2H); 7.07(t, J=7.6Hz, 1H); 7.20–7.35(a.c., 3H); 7.63 (d, J=8.5Hz, 1H); 7.71(d, J=8.6Hz, 1H); 7.90(s. 1H) ($CDCl_3$) |
| 43a | H | H | F | H | H | N | C—CH═CH—CH═CH | | N | HCl 208–209° C. | 2574, 2482, 1510, 1231, 745 KBr | 1.80(m, 2H); 2.11(quin., J=7.2Hz, 2H); 2.69(m, 1H); 2.83(m, 1H); 3.10–3.20(a.c., 3H); 3.52(m, 1H); 3.71 (m, 1H); 3.88(m, 1H); 4.80(t, J=6.3Hz, 2H); 6.11(s, 1H); 7.19(m, 2H); 7.41(m, 2H); 7.50(m, 2H); 7.91(m, 2H); 11.07(b.a., 1H) (DMSO-$d_6$) |

TABLE 2-continued

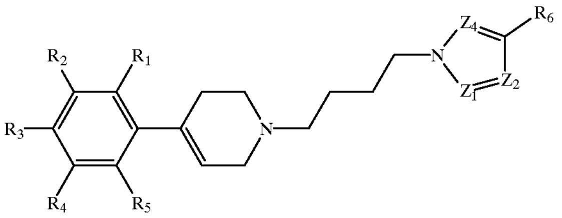

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1H$-RMN (300 MHz), δ (solvent) |
|---|---|---|---|---|---|---|---|---|---|---|---|---|
| 44a | H | H | F | H | H | N | C—CH=CH—CH=CH | | N | 76–77° C. | 2913, 1511, 1470, 1380, 1327, 1224, 1172, 1132, 851, 826, 757 KBr | 1.60(quin., J=7.5Hz, 2H); 2.19(quin., J=8.2Hz, 2H); 2.41–2.59(a.c., 4H); 2.64(t, J=5.7Hz, 2H); 3.08(m, 2H); 4.77(t, J=7.0Hz, 2H); 5.95(m, 1H); 6.97(t, J=8.8Hz, 2H); 7.25–7.40(a.c., 4H); 7.85(m, 2H) ($CDCl_3$) |
| 45a | H | H | F | H | H | N | N | CH=CH—CH=CH—C | | HCl 204–205° C. | 2928, 2680, 2573, 2559, 1515, 1454, 1272, 1242, 1224, 1166, 819, 745 KBr | 1.81(m, 2H); 1.99(m, 2H); 2.67(m, 1H); 2.84(m, 1H); 3.10–3.20(a.c., 3H); 3.53(m, 1H); 3.72(m, 1H); 3.90 (m, 1H); 4.76(t, J=6.9Hz, 2H); 6.12(s. 1H); 7.19 (t, J=8.8Hz, 2H); 7.39(t, J=7.6Hz, 1H); 7.45–7.60(a.c., 3H); 7.94(d, J=8.3Hz, 2H); 8.03(d, J=8.3Hz, 2H); 11.04 (b.a., 1H) (DMSO-$d_6$) |
| 46a | H | H | F | H | H | N | N | CH=CH—CH=CH—C | | 88–90° C. | 2939, 1510, 1229, 1209, 1164, 744 KBr | 1.58(quin., J=7.5Hz, 2H); 2.07(quin, J=7.5Hz, 2H); 2.40–2.50(a.c., 4H); 2.61(m, 2H); 3.05(m, 2H); 4.66 (t, J=7.0Hz, 2H); 5.95(m, 1H); 6.96(t, J=8.8Hz, 2H); 7.23–7.38(a.c., 3H); 7.44(m, 1H); 7.52(m, 1H); 8.04 (d, J=8.3Hz, 1H) ($CDCl_3$) |
| 47a | H | H | Cl | H | H | N | CH | Cl | CH | HCl 172–173° C. | 3068, 2948, 1491, 1445, 1320, 1308, 1096, 968, 809, | 1.71(m, 2H); 1.80(m, 2H); 2.70(m, 1H); 2.83(m, 1H); 3.15–3.30(a.c., 3H); 3.44(m, 1H); 3.72(m, 1H); 3.89 (m, 1H); 4.11(t, J=6.5Hz, 2H); 6.20(s, 1H); 7.41(sys. AB, $J_{AB}$=8.8Hz, 2H); 7.48(Syst. AB, $J_{AB}$= 8.8Hz, 2H); 7.52(s, 1H); 8.04(s, 1H); 10.98(b.a., 1H) (DMSO-$d_6$) |
| 48a | H | H | H | H | H | N | CH | H | CH | HCl 180–181° C. | 2955, 2929, 2530, 1445, 965, 761, 745 KBr | 1.70–1.90(a.c., 4H); 2.69(m, 1H); 2.89(m, 1H); 3.10–3.20(a.c., 3H); 3.53(m, 1H); 3.70(m, 1H); 3.91(m, 1H); 4.15(t, J=6.5Hz, 2H); 6.16(m, 1H); 6.23(m, 1H); 7.28–7.50(a.c., 6H); 7.78(m, 1H); 11.26(b.a., 1H) (DMSO-$d_6$) |
| 49a | H | H | H | H | H | CH | N | H | N | HCl 122–123° C. | 2937, 2370, 1503, 1276, 1142, 774, 755 KBr | 1.74(m, 2H); 1.84(m, 2H); 2.72(m, 1H); 2.87(m, 1H); 3.10–3.20(a.c., 3H); 3.54(m, 1H); 3.73(m, 1H); 3.88 (m, 1H); 4.22(t, J=6.6Hz, 2H); 6.15(s, 1H); 7.27–7.70 (a.c., 3H); 7.47(m, 2H); 7.97(s, 1H); 8.59(s, 1H); 11.20(b.a., 1H) (DMSO-$d_6$) |
| 50a | H | H | H | H | H | CPh | N | H | CH | HCl 170–171° C. | 2930, 2554, 1469, 1459, 1444, | 1.62–1.78(a.c., 4H); 2.75(m, 2H); 3.00(m, 2H); 3.25 (m, 2H); 3.69(m, 2H); 4.08(t, J=6.7Hz, 2H); 6.13(s, 1H); 7.07(s, 1H); 7.24–7.40(a.c., 3H); 7.42–7.52(a.c., |

TABLE 2-continued

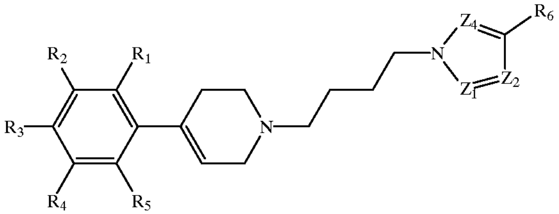

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| | | | | | | | | | | | 1278, 1075, 774, 762, 749, 732, 711, 702, 690 KBr | 6H); 7.62(Syst. AB, $J_{AB}$= 7.6Hz, 2H) (DMSO-$d_6$) |
| 51a | H | H | H | H | H | CH | CH | H | CH | HCl 197–199° C. | 2930, 2482, 1448, 1280, 1090, 732 KBr | 1.60–1.80(a.c., 4H): 2.70m, 1H); 2.84(m, 1H); 3.08–3.22(a.c., 3H); 3.50(m, 1H); 3.71(m, 1H); 3.86–3.96 (a.c., 3H): 5.97(t, J=2.1Hz, 2H); 6.16(m, 1H); 6.76 (t, J=2.1Hz, 2H); 7.25–7.50(a.c., 5H); 10.74(b.a., 1H) (DMSO-$d_6$) |
| 52a | H | H | H | H | H | CH | CH | H | CH | 58–60° C. | 2928, 1498, 1280, 1262, 1137, 1087, 1060, 747, 723, 691 KBr | 1.58(m, 2H); 1.84(m, 2H); 2.47(t, J=7.5Hz, 2H); 2.58 (m, 2H); 2.68(m, 2H); 3.13(m, 2H); 3.92(t, J=7.1Hz, 2H); 6.06(m, 1H); 6.15(t, J=2.2Hz, 2H); 6.67 (t, J=2.2Hz, 2H); 7.24–7.42(a.c., 5H) ($CDCl_3$) |
| 53a | H | H | H | H | H | N | CCl | CH═CH—CH═CH—C | | oil | 2939, 1495, 1467, 1338, 745 film | 1.58(quin, J=7.6Hz, 2H); 1.99(quin, J=7.6Hz, 2H); 2.47(m, 2H); 2.55(m, 2H); 2.65(m, 2H); 3.10(m, 2H); 4.36(t, J=7.1Hz, 2H); 6.04(m, 1H); 7.18–7.42(a.c., 8H); 7.67(d, J=7.6Hz, 1H) ($CDCl_3$) |
| 54a | H | H | H | H | H | N | CCl | CH═CH—CH═CH—C | | HCl 164–165° C. | 3460, 2940, 2550, 1338, 743 KBr | 1.80(m, 2H); 1.90(m, 2H); 2.70(m, 1H); 2.87(m, 1H); 3.07–3.22(a.c., 3H); 3.52(m, 1H); 3.71(m, 1H); 3.87 (m, 1H); 4.43(t, J=6.6Hz, 2H); 6.14(s, 1H); 7.20–7.52 (a.c., 7H); 7.65(m, 1H); 7.7(m, 1H); 11.16(b.a., 1H) (DMSO-$d_6$) |
| 55a | H | H | OH | H | H | $CCH_3$ | N | Cl | CCl | HCl 216–217° C. | 3062, 2561, 1516, 1248 KBr | 1.69(m, 2H); 1.75(m, 2H); 2.33(s, 3H); 2.68(m, 1H); 2.79(m, 1H); 3.14(a.c., 3H); 3.55(m, 1H); 3.68(m, 1H); 3.87–4.00(a.c., 3H), 5.97(s, 1H); 6.77(Syst. AB, J=8.8Hz, 2H); 7.28(Syst. AB, J=8.8Hz, 2H); 9.62 (s, 1H); 10.82(b.a., 1H) (DMSO-$d_6$) |
| 56a | H | H | H | H | H | CH | N | Cl | CCl | HCl 166–167° C. | 2336, 1254 KBr | 1.75(a.c., 4H); 2.70(m, 1H); 2.87(m, 1H); 3.17(a.c., 3H); 3.56(m, 1H); 3.74(m, 1H); 3.87–4.15(a.c., 3H), 6.17(s, 1H); 7.27–7.40(a.c., 3H); 7.47(m, 2H); 7.91(s, 1H); 11.02(b.a., 1H) (DMSO-$d_6$) |
| 57a | H | H | F | H | H | CH | N | H | N | Citrate 132–133° C. | 1720, 1709, 1513, 1225, | 1.90(m, 2H); 2.08(quint., J=7.5Hz, 2H); 2.86(AB, J=15.5Hz, 4H); 2.93(b.a., 2H); 3.29(m, 2H); 3.54(t, |

TABLE 2-continued

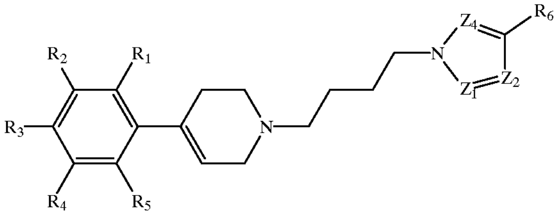

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1H$-RMN (300 MHz), δ (solvent) |
|---|---|---|---|---|---|---|---|---|---|---|---|---|
| | | | | | | | | | | | 1193, 1166, 1133 KBr | J=5.9Hz, 2H) 3.93(b.a., 2H); 4.43(t, J=6.6Hz, 2H); 6.17(b.a., 1H); 7.19(m, 2H); 7.59(m, 2H); 8.10(s, 1H); 8.60(s, 1H) ($MeOH-d_4$) |
| 58a | H | H | Br | H | H | CH | N | H | N | 113–115° C. | 2939, 2773, 2736, 1509, 1490, 1380, 1271, 1140, 1071, 1006, 961, 844, 827, 800, 680 KBr | 1.55(m, 2H); 1.95(m, 2H); 2.40–2.55(a.c., 4H); 2.64 (m, 2H); 3.08(m, 2H); 4.20(t, J=7.1Hz, 2H); 6.03(m, 1H); 7.22(AB, J=8.5Hz, 2H); 7.40(AB, J 7.93(s, 1H); 8.05(s, 1H) ($CDCl_3$) |
| 59a | H | H | Br | H | H | CH | N | H | N | HCl 162–164° C. | 3066, 2937, 2479 (b.a.) 1514, 1146, 1012, 802 KBr | 1.76(m, 2H); 1.84(m, 2H); 2.71(m, 1H); 2.85(m, 1H); 3.17(a.c., 3H); 3.55(m, 1H); 3.74(m, 1H); 3.80(m, 1H), 4.23(t, J=6.6Hz, 2H); 6.22(s, 1H); 7.42(Syst. AB, J=8.1Hz, 2H); 7.56(Syst. AB, J=8.1Hz, 2H); 7.98 (s, 1H); 8.60(s, 1H) ($DMSO-d_6$) |
| 60a | H | H | Cl | H | H | CH | N | H | N | 101–103° C. | 2930, 2775, 2737, 1509, 1493, 1381, 1271, 1141, 1091, 1010, 961, 847, 828, 680 KBr | 1.56(quint, J=7.5Hz, 2H); 1.97(quint, J=7.5Hz, 2H); 2.40–2.70(a.c., 4H); 2.66(t, J=5.7Hz, 2H); 3.10(d, J=3 Hz, 2H), 4.21(t, J=7.0Hz, 2H); 6.04(s, 1H); 7.20–7.35 (m, 4H); 7.94(s, 1H); 8.06(s, 1H) ($CDCl_3$) |
| 61a | H | H | Cl | H | H | CH | N | H | N | HCl 165–166° C. | 2951, 2505 (b.a.) 1502, 1494, 1275, 1136, 1098, 1013, 810, 686 KBr | 1.73(m, 2H); 1.83(m, 2H); 2.70(m, 1H); 2.85(m, 1H); 3.10–3.20(a.c., 3H); 3.54(m, 1H); 3.73(m, 1H); 3.88 (m, 1H); 4.22(t, J=6.6Hz, 2H); 6.20(s, 1H); 7.42(syst. AB, J=8.6Hz, 2H); 7.49(Syst. AB, J=8.6Hz, 2H); 7.97 (s, 1H): 8.59(s, 1H); 11.17(b.a., 1H) ($DMSO-d_6$) |
| 62a | H | H | Cl | H | H | CPh | N | H | CH | oil | 1445, 1379, 1271, 774, 681 film | 1.48(m, 2H); 1.80(m, 2H); 2.36(t, J=7.4Hz, 2H); 2.47 (m, 2H); 2.59(m, 2H); 3.04(d, J=3Hz, 2H), 4.03(t, J=7.4Hz, 2H); 6.01(s, 1H); 7.01(d, J=1.2Hz, 1H); 7.11(d, J=1.2Hz, 1H); 7.27(m, 4H); 7.35–7.60(a.c., 5H) ($CDCl_3$) |
| 63a | H | H | Cl | H | H | CPh | N | H | CH | HCl 70° C. (hygrosc.) | 2935, 2695, 2591, 1493, 1094, 777, 702 KBr | 1.65(m, 2H); 1.80(m, 2H); 2.67(m, 1H): 2.82(m, 1H); 3.05–3.21(a.c., 3H); 3.55(m, 1H); 3.69(m, 1H); 3.88 (m, 1H), 4.20(t, J=6.6Hz, 2H); 6.18(s, 1H); 7.40(Syst. AB, J=8.7Hz, 2H); 7.47(Syst. AB, J=8.7Hz, 2H); 7.60– |

TABLE 2-continued

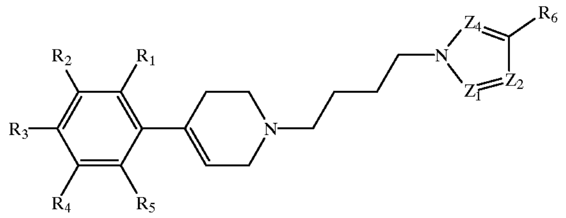

| Ex. | $R_1$ | $R_2$ | $R_3$ | $R_4$ | $R_5$ | $Z_1$ | $Z_2$ | $R_6$ | $Z_4$ | Salt/m.p. | IR $cm^{-1}$ | $^1$H-RMN (300 MHz), δ (solvent) |
|---|---|---|---|---|---|---|---|---|---|---|---|---|
| | | | | | | | | | | | | 7.880(a.c., 5H); 7.83(s, 1H); 7.96(s, 1H) (DMSO-$d_6$ + TFA) |
| 64a | H | H | H | H | H | $CCH_3$ | CH | H | $CCH_3$ | oil | 2929, 1408, 1299, 746, 693 film | 1.65(a.c., 4H); 2.23 (s, 6H); 2.48(m, 2H); 2.58(m, 2H); 2.69(m, 2H); 3.15(m, 2H); 3.76(t, J=7.2Hz, 2H); 5.76 (s, 2H): 6.06(s, 1H); 7.20–7.40(a.c., 5H) ($CDCl_3$) |
| 65a | H | H | H | H | H | $CCH_3$ | CH | H | $CCH_3$ | HCl 178–180° C. | 3434 (b.a.), 2935, 2560, 1443, 1405, 1298, 748, 692 | 1.56(m, 2H); 1.77(m, 2H); 2.15(s, 6H); 2.70(m, 1H); 2.84(m, 1H); 3.08–3.22(a.c., 3H); 3.59(m, 1H); 3.70–3.80(a.c., 3H); 3.93(m, 1H); ); 5.59(s, 2H); 6.17(s, 1H); 7.25–7.50(a.c., 5H); 10.72(b.a., 1H) (DMSO-$d_6$) |
| 66a | H | H | Cl | H | H | $CCH_3$ | CH | H | $CCH_3$ | 86–88° C. | 2933, 1493, 1413, 1376, 1300, 750 film | 1.65(a.c., 4H); 2.24(s, 6H); 2.48(m, 2H); 2.54(m, 2H); 2.69(m, 2H); 3.15(m, 2H); 3.77(t, J=7.1Hz, 2H); 5.77 (s, 3H); 6.06(s, 1H); 7.30(m, 4H) ($CDCl_3$) |
| 67a | H | H | Cl | H | H | $CCH_3$ | CH | H | $CCH_3$ | HCl 182–184° C. | 3432 (b.a.), 2936, 258-, 1495, 1410, 1298, 1097, 804, 752 KBr | 1.56(m, 2H); 1.76(m, 2H); 2.14(s, 6H); 2.70(m, 1H); 2.84(m, 1H); 3.00–3.28(a.c., 3H); 3.58(m, 1H); 3.69–3.77(a.c., 3H); 3.92(m, 1H); ); 5.58(s, 2H); 6.22(s, 1H); 7.42(AB, J=8.6, 2H); 7.50(AB, J=8.6, 2H); 10.65 (b.a., 1H) (DMSO-$d_6$) |
| 68a | H | H | Cl | H | H | CH | CH | H | CH | 102–104° C. | 2931, 1492, 1280, 1090, 967, 828, 727 KBr | 1.56(t, J=7.5Hz, 2H); 1.84(t, J=7.4Hz, 2H); 2.46 (t, J=7.5Hz, 2H); 2.53(m, 2H); 2.66(t, J=5.6Hz, 2H); 3.12(m, 2H); 3.92(t, J=7.1Hz, 2H); 6.05(m, 1H): 6.15 (d, J=1.8Hz, 2H); 6.66(d, J=1.8Hz, 2H); 7.26AB, J=8.4, 2H); 7.30(AB, J=8.4, 2H) ($CDCl_3$) |
| 69a | H | H | Cl | H | H | CH | CH | H | CH | HCl 194–195° C. | 2937, 2479, 1492, 1282, 1096, 810, 737 KBr | 1.72(m, 4H); 2.65(m, 1H); 2.87(m, 1H); 3.08–3.22 (a.c., 3H); 3.52(m, 1H); 3.70(m, 1H); 3.80–4.00(a.c., 3H); 5.96(t, J=2.1Hz, 2H); 6.19(s, 1H); 6.76(t, J=2.1Hz, 2H); 7.42(AB, J=8.6Hz, 2H); 7.48(AB, J=8.6Hz, 2H); 11.12(b.a., 1H) (DMSO-$d_6$) |
| 70a | H | H | Cl | H | H | CH | N | H | N | Citrate 133° C. | 3384 (b.a.), 3200–2200 (b.a.) 1726, 1702, 1594, 1432, 1221, 1131, 802 KBr | 1.54(m, 2H); 1.83(m, 2H); 2.54(Syst. AB, J=15Hz, 2H); 2.63(Syst. AB, J=15Hz, 2H); 2.82(m, 2H); 3.03 (m, 2H); 3.20–3.50(a.c., 4H); 4.21(t, J=6.8Hz, 2H); 6.20(s, 1H); 7.40(Syst. AB, J=8.8Hz, 2H); 7.48(Syst. AB, J=8.8Hz, 2H); 7.97(s, 1H); 8.52(s, 1H) (DMSO-$d_6$) |

EBIOLOGICAL ASSAYS

The analgesic activity of the products object of the invention have been studied in several assays using the Swiss albino mice as the experimental animal. The assay of contortions induced by phenylbenzoquinone, the hot-plate assay and the hot-point assay are now described. The examples that are presented by way of illustration describe some of the pharmacological assays and should not limit the scope of the invention in any way.

The assay of contortions induced by phenylbenzoquinone was carried out following the method described by E. Siegmund et al. (Proc. Soc. Exp. Biol. Med. 95: 729–731, 1957). In this assay the mice received [th]e product orally or sub-cutaneously (s.c.) and after 60 minutes (after oral administration) or after 30 minutes (after s.c. administration) they received an intraperitoneal (i.p.) injection of an 0.02% aqueous solution of phenylbenzoquinone, at a dosage of 10 ml/kg. The degree of analgesic was expressed as a percentage of the contortions with respect to the control group at each one of the dosages assayed. Using the results tained the effective dose-50 (ED-50) was calculated, that is to say the dose able to inhibit by 50% the contortions induced by phenylbenzoquinone.

The hot-plate assay was carried out following the method described by M. Ocaña et al. (Europ.J.Pharmacol. 186: 377–378, 1990). The product under study was administered s.c. or i.p. and 30 minutes later the analgesic effect was registered. For this the animals were placed on a metallic surface kept at 50° C. or 55° C. and the time registered (latency) until the licked their hind legs and a jump. The analgesic activity was calculated at each dose, comparing the potency of the treated group with the control group. Using the results obtained the ED-50 was calculated.

The assay of withdrawal of the tail from a hot spot (tail flick) was carried out following the method described by M. Ocaña et al. (Br. J. Pharmacol. 110: 1049–1054, 1993). The mice were introduced into an immobiliser and placed on the tail-flick apparatus (LI7100, Letica, S.A). A beam of light was focussed on the tail, at 4 cm from the tip, and the latency for withdrawal of the tail automatically registered. Ten minutes before administering the product of the study the basal latency was registered.

After the product had been administered s.c. the tail withdrawal latencies at 10, 20, 30, 40, 45, 60, 90 and 120 minutes were registered. For each animal the area below curve of the latency was calculated during the time period following the method described by R. J. Tallarida and R. B. Murray (Manual of pharmacologic calculations with computer programs, Springer-Verlag, Berlin, p. 297, 1987). The degree of analgesic of each dosage was calculated comparing the area under curve of latency of the group treated with the medicament with the control group. Using these data the ED-50 was calculated.

The products object of the invention have a notable analgesic activity in the assay of contortions induced by phenylbenzoquinone. Several products have activity of the same order as morphine and clearly better that the products that inhibit biosynthesis of prostaglandins, such as aspirin and dipirone (see table 3).

The analgesic activity has also been demonstrated in the hot-plate assay, considered as a demonstration of analgesic action at the central nervous system level (see table 4).

The analgesic activity has also been demonstrated in the hot-beam assay applied to the mouse's tail, finding a good correspondence between the results obtained in the assay of the hot-plate and the assay of the calorific beam (see table 5).

Furthermore, the capacity of the products object of the invention for exhibiting synergistic analgesic activity with other analgesics, for example, pentazocine, has also been demonstrated. This has been shown for the compound of example 47a (see table 6). Effectively, the latency time in responding licking of the paws when the mice were placed on the hot-plate at 55° C., is much greater after the combined treatment with the compound of example 47a and pentazocine than the sum of the latencies of each one of the treatments carried out separately.

In summary, the products object of the invention have shown a clear analgesic activity in different assays, such as phenylbenzoquinone, hot-plate and calorific beam applied to the tail of the mouse. The activity of these products has been clearly superior to that of the inhibitors of the biosynthesis of prostaglandins such as aspirin and dipirone, and the activity has been shown to of the order of that of morphine. Furthermore, 5 the capacity for forming synergistic combinations with other analgesics has been demonstrated, as can be seen for the case of the compound of example 47a administered along with pentazocine in the hot-plate assay for mice.

TABLE 3

Analgesic activity in the assay of contortions induced by phenylbenzoquinone in mouses

| PRODUCT | ED-50 (mg/kg) Oral route | ED-50 (mg/kg) S.C. route |
|---|---|---|
| Example 5 | 20 | 28 |
| Example 6 | 80 | 34 |
| Example 33a | 30 | 2 |
| Example 35a | 37 | 1 |
| Example 38a | 5 | 1 |
| Example 41a | 58 | 6 |
| Example 47a | 19 | 26 |
| Example 48a | 38 | 1 |
| Example 49a | 2 | 1 |
| Example 50a | 10 | 2 |
| Example 5la | 9 | 3 |
| Example 59a | 13 | 2 |
| Example 61a | 22 | 2 |
| Example 63a | 44 | 33 |
| Morfine | 4 | 1 |
| Dipirone | 223 | 24 |
| Aspirin | 100 | 80 |

TABLE 4

Analgesic activity in the hot-plate assay (55° C.) in mouses

| PRODUCT | ED-50 (mg/kg, sc) |
|---|---|
| Example 38a | 7 |
| Example 47a | 89 |
| Example 48a | 5 |
| Example 49a | 4 |
| Example 50a | 58 |
| Example 51a | 2 |
| Example 59a | 43 |
| Example 61a | 48 |
| Morfina | 2 |

TABLE 5

| Analgesic activity in the calorific beam assay in mouse's tail. | |
|---|---|
| PRODUCT | ED-50 (mg/kg, sc) |
| Example 51a | 5 |
| Example 59a | 60 |
| Example 63a | 70 |
| Morfine | 4 |

TABLE 6

| Analgesic activity in the hot plate assay in mouse. | | |
|---|---|---|
| PRODUCT | DOSE (mg/kg, ip) | Δ Latency (Seconds) |
| Example 47a | 40 | 5 |
| Pentazocine | 10 | 6 |
| Example 47a<br>+<br>Pentazocine | 40<br>+<br>10 | 20 |

What is claimed is:

1. A method of treating acute pain, neuropathic pain or nociceptive pain in a mammal which comprises administering to a patient in need thereof an effective amount of a derivative of tetrahydropyridines of formula (I)

(I)

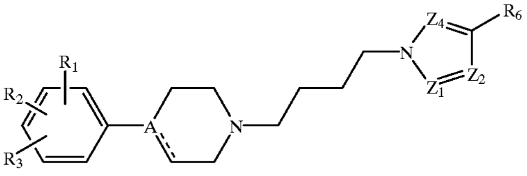

where $R_1$, $R_2$ and $R_3$ are identical or different and are selected from hydrogen, $C_1$–$C_4$ alkyl group, trifluoroethyl radical, hydroxyl or alkoxyl radical; and two adjacent radicals can form part of a six-membered aromatic ring;

A is selected from a carbon atom or a carbon atom bound to a hydroxyl group (C—OH); wherein when A is a carbon atom the dotted line (- - -) represents a bond, and when A is a carbon atom bound to a hydroxyl group (C—OH) the dotted line (- - -) represents no bond;

$Z_1$, is a nitrogen atom or a substituted carbon atom represented by the formula C—$R_4$;

$Z_2$ is a nitrogen atom or a substituted carbon atom represented by the formula C—$R_5$;

$Z_4$ is a nitrogen atom or a substituted carbon atom represented by the formula C—$R_7$;

with the condition that $Z_1$; $Z_2$ and $Z_4$ taken together can represent at most, two nitrogen atoms; and $R_4$, $R_5$, $R_6$ and $R_7$, are identical or different and are selected from hydrogen, halogen, $C_1$–$C_4$ alkyl group, aryl or substituted aryl group, and two adjacent radicals can form part of a six-membered aromatic ring;

or physiologically acceptable salts thereof.

2. The method as claimed in claim 1, wherein $R_1$, $R_2$ and $R_3$ are selected from hydrogen, fluorine, chlorine, bromine, trifluoromethyl, hydroxyl, methoxyl, methyl, ethyl, propyl, isopropyl, sec-butyl and a tert-butyl radical.

3. The method as claimed in claim 1, wherein $R_1$, $R_2$ and $R_3$ are selected so that two adjacent radicals can form part of a six-membered aromatic ring.

4. The method as claimed in claim 1, wherein $R_4$, $R_5$, $R_6$ and R7 are selected from hydrogen, fluorine, chlorine, bromine, trifluoromethyl, hydroxyl, methoxyl, methyl, ethyl, propyl, isopropyl, sec-butyl, tert-butyl, unsubstituted phenyl, or a substituted phenyl wherein the substituent is selected front halogen atoms.

5. The method as claimed in claim 1, wherein $R_4$, $R_5$, $R_6$ and $R_7$ are selected so wt two adjacent radicals form part of a six-membered aromatic ring.

6. The method as claimed in claim 1, further comprising an analgesic used for the treatment of pain.

7. The method as claimed in claim 1, wherein the compound of formula (I), is selected from the group consisting of 4-chloro-1-[4-(4hydroxy-4-phenyl-1-piperidinyl)butyl]-1-pyrazole;

4,5chloro-1-[4(4-hydroxy-phenyl-1-piperidinyl)butyl]-2-ethyl-1H-imidazole;

1-[4-(4hydroxy[]phenyl-1 -piperidinyl)butyl]-1H-benzimidazole;

1-[(4hydroxy-phenyl-1 -piperidinyl)butyl]-1H-1,2,4-thiazole;

4-chloro-1-{4-[4chlorophenyl)-4-hydroxy-1-piperidinyl]butyl}-1H-pyrazole;

4,5-dichloro-1-{4-[4-hydroxy-4-(chlorophenyl)-1 -piperidinyl]butyl}- 2-methyl-1-H-imidazole;

4-chloro-1-{4-[4-hydroxy-4-(3-trifluoromethylphenyl)-1-piperidinyl]-butyl}-1H-pyrazole 4,5-dichloro-1-{4-[4-hydroxy-4-(3-trifluoromethylphenyl)-1-piperidinyl]-butyl}-2H-imidazole;

4,5-dichloro-1-{4-[4-(4-fluorophenyl)-4-hydroxy-1-piperidinyl]-butyl}-2H-methyl-1-H-imidazole;

1-[4-(4-hydroxy-4-phenyl-1-piperidinyl)-butyl]-1H-indole 4,5-dichloro-1-{[4-hydroxy-(fluorophenyl)-4-hydroxy-1-piperidinyl]butyl}-2-methyl-1-H-imidazole;

1-[4(4-hydroxy-4-phenyl-1-piperidinyl)butyl]-1H-indole 4,5-dichloro-1-{4-[4hydroxy 4-(4-methylphenyl)1-piperyl]-butyl}-2-methyl-1H-imidazolo;

1-[-4-(4-hydroxy-4-phenyl-1-piperidinyl)butyl]-1H-pyrazole;

1-[-4-(4-hydroxy-4-phenyl-1-piperidinyl)butyl]-1H-imidazole;

2-[-4-(4-hydroxy-4-phenyl-1-piperidinyl)butyl]-2H-imidazole;

4-chloro-1-{4-[4-hydroxy-4-(4-methylphenyl)-1-(piperidinyl)]-butyl}-1H-pyrazole;

4-chloro-1-{4-[4-hydroxy-4-(4-methyoxphenyl)-1-(piperidinyl)]-butyl}-1H-pyrazole;

1-[4(4hydroxy-4-phenyl-1-piperidinyl)butyl]-2-phenyl-1H-imidazole 1-{4-[4-hydroxy-4-(4-methylphenyl-1-piperidinyl]butyl}-1H-benzimidazole;

4,5-diphenyl-1-[4-(4-hydroxy-4-phenyl-1-piperidinyl)butyl]-1H -imidazole 4-chloro-1-{4-[4-hydroxy-4-(1-naphthyl)-1-piperidinyl]butyl}-1H-pyrazole;

4-chloro-1-{4-[4-hydroxy4-(2-naphthyl-1-piperidinyl]-butyl}-1H-pyrazole;

4-chloro-1-{4-[4-phenyl-1-(1,2,3,6-tetrahydropyridinyl)]-butyl}-1H-pyrazole;

1-{4-[4phenyl-1-(1,2,3,6-tetrahydropyridinyl)]butyl}-1H-benzimidazole;

1-{4-[4phenyl-1(1,2,3,6-tetrahydropyridinyl)]butyl}-1H-1,2,4-triazole;

4chloro-1-{4-[4-(4-chlorophenyl)-1-(1,2,3,6-tetrahydro-pyridinyl)]butyl}-1H-pyrazole;

4,5-dichloro-1-{4-[4-(4-chlorophenyl)-1-(1,2,3,6-tetrahydropyridinyl)]-butyl-}-2-metbyl-1H-imidazole;

4chloro-1-{4-[4-(3-trifuoromethylphenyl)-1-(1,2,3,6-tetrahydropyridinyl)]-butyl-}-1H-pyrazole;

4,5-dichloro-2-methyl-1-{4-[4-(3-trifluoromethylphenyl)-1-(1,2,3,6tetahydro-pyridinyl)]-butyl}-1H-imidazole;

4-chloro-1-{4-[4-(1-naphthyl)-1-(1,2,3,6-tetrahydropyridinyl]butyl}-1H-pyrazole;

4chloro-1-{4-[4-(2-naphtyl)-1-(1,2,3,6-tetrahydropyridinyl)]butyl}-1H-pyrazole;

1-{2-[4-(4-fluorophenyl)-1-(1,2,3,6-tetrahydropyridinyl)]etil}-1H-benzimidazole;

1-{4-[4-(4-phenyl)-1-(1,2,3,6-tetrahydropyridinyl)]butyl}-1H-benzimidazole hydrochloride;

1-{4-[4-(4-fluorophenyl)-1-(1,2,3,6-tetrahydropyridinyl)]butyl}-1H-benzimidazole;

1-{4-[4-(4-fluorophenyl)-1-(1,2,3,6-tetrahydropyridinyl)]butyl}-1H-bencimidazole hydrochloride;

4,5-dichloro-2-methyl-1-{4-[4(3-trifluoromethylphenyl)-1-(1,2,3,6-tetrahydropyridinyl)]-butyl}-1H-imidazole-hydrochloride;

4-chloro-1-{4-[4-(4-fluorophenyl)-1-(1,2,3,6)-tetrahydropyridinyl)]butyl}-1H-pyrazole hydrochloride;

1-{4-[1-phenyl-1-(1,2,3,6-tetrahydropyridinyl)]butyl}-1H-imidazole hydrochloride;

4,5-dichloro-1-{4-[4-fluorophenyl)-1-(1,2,3,6-tetrahydropyridinyl)]butyl}-2-methyl-1H-imidazole hydrochloride;

4-(chlorophenyl)-1-{4-[4-phenyl-1-(1,2,3,6-tetrahydropyridinyl)]butyl}-1H-pyrazole hydrochloride;

4-(4-chlorophenyl)-1-{4-[4-phenyl-1-(1,2,3,6-tetrahydropyridinyl)]butyl }-1H-pyrazole;

1-{4-[4-(4-fluorophenyl)-1-(1,2,3,6-tetrahydropyridinyl)]butyl}-1H-triazole hydrochloride;

1-{4-[4-(4-fluorophenyl)-1-(1,2,3,6-tetrahydropyridinyl)]butyl}-1H-triazole;

1-{4-[4-(4-fluorophenyl)-1-(1,2,3,6-tetrahydropyridinyl)]butyl}-2-methyl-1H-benzimidazole;

1-{4-[4-(4-fluorophenyl)-1-(1,2,3,6-tetrahydropyridinyl)]butyl}-1H-imidazole;

2-{4-[4-(4-fluorophenyl)-1-(1,2,3,6-tetrahydropyridinyl)]butyl}-2H-imidazole;

2-{4-[4-(4-fluorophenyl)-1-(1,2,3,6-tetrahydropyridinyl)]butyl}-2H-benzotriazole hydrochloride;

2-{4-[4-(4-fluorophenyl)-1-(1,2,3,6-tetrahydropyridinyl)]butyl}-2H-benzotriazole;

1-{4-[4-(4-fluorophenyl)-1-(1,2,3,6-tetrahydropyridinyl)]butyl}-1H-benzotriazole hydrochloride;

1-{4-[4-(4-fluorophenyl)-1-(1,2,3,6-tetrahydropyridinyl)]butyl}-1H-benzotriazole;

4chloro-1-{4-[4(4-chlorophenyl)-1-(1,2,3,6-tetrahydropyridinyl]butyl}-1H-pyrazole hydrochloride;

1-{4-[4-(4-phenyl)-1-(1,2,3,6-tetrahydropyridinyl)]butyl}-1H-pyrazole hydrochloride;

1-{4-[4-(4-phenyl)-1-(1,2,3,6-tetrahydropyridinyl)]butyl}-1H-triazole hydrochloride;

2-phenyl-1-{4-[-4-1-(1,2,3,6-tetrahydropyridinyl)]-butyl}-1H-imidazole hydrochloride;

1-{4-[4-(4-phenyl)-1-(1,2,3,6-tetrahydropyridinyl)]butyl}-1H-pyrrrole hydrochloride;

1-{4-[4-(4-phenyl)-1-(1,2,3,6-tetrahydropyridinyl)]butyl}-1H-pyrrole;

4-(4-chlorophenyl)-1-[4-(4hydroxy-4-phenyl-1-piperdinyl)butyl]1H-pyrazole;

1-{4-[4-(4-fluorophenyl)-4-hydroxy-1-piperidinyl]butyl}-1H-benzimidazole;

4-chloro-1-{4-[4-hydroxy-4-(3-trifluoromethylphenyl)-1-piperidinyl]butyl}-1H-pyrazole;

1-{4-[4-(4-fluorophenyl)-4-hydroxy-1-piperidinyl]butyl}-1H-imidazole;

2-{4-[4-(4-fluorophenyl)-4-hydroxy-1-piperidinyl]butyl}-2H-imidazole;

2-{4-[4-(4-fluorophenyl)-4-hydroxy-1-piperidinyl]butyl}-2H-benzotriazole;

1-{4-[4-(4-fluorophenyl)-4-hydroxy-1-piperidinyl]butyl}-1H-benzotrizole;

3-chloro-1-{4-[4-phenyl-1-(1,2,3,6-tetrahydropyridinyl)]butyl}-1H-imidazole;

3-chloro-1-{4-[4-phenyl-1-(1,2,3,6-tetrahydropyridinyl)]butyl}-1H-imidazole hydrochloride;

1-{4-[4-hydroxy-4-(4-fluorophenyl)-1-piperidinyl]butyl}-1H-triazole;

1-{4-[4-hydroxy-4-(4-chlorophenyl)-1-piperidinyl]butyl}-1H-triazole;

4,5-dichloro-1-{4-[4-(4-phenyl-1-(1,2,3,6-tetrahydropyridinyl)]butyl}-1H-imidazole hydrochloride;

1-{4-[4-(4-fluorophenyl)-1-(1,2,3,6-tetrahydropyridinyl)]butyl}-1H-triazole citrate;

1-{4-[4-(4-bromophenyl)-1-(1,2,3,6-tetrahydropyridinyl)]butyl}-1H-triazole;

1-{4-[4-(4-bromophenyl)-1-(1,2,3,6-tetrahydropyridinyl)]butyl}-1H-triazole hydrochloride;

1-{4-[4-(4-chlorophenyl)-1-(1,2,3,6-tetrahydropyridinyl)]butyl}-1H-triazole;

1-{4-[4-(4-chlorophenyl)-1-(1,2,3,6-tetrahydropyridinyl)]butyl}-1H-triazole hydrocloride;

2-phenyl-1-{4-[4-(4-chlorophenyl)-1-(1,2,3,6-tetrahydropyridinyl)]butyl}-1H-imidazole;

2-phenyl-1-{4-[4-(4-chlorophenyl)-1-(1,2,3,6-tetrahydropyridinyl)]butyl}-1H-imidazole hydrochloride;

2,5-dimethyl-1-{4-[4-(4-phenyl)-1-(1,2,3,6-tetrahydropyridinyl)]butyl}-1H-pyrrole;

2,5-dimethyl-1-{4-[4-(4-phenyl)-1-(1,2,3,6-tetrahydropyridinyl)]butyl}-1H-pyrrole hydrochloride;

2,5-dimethyl-1-{4-[4-(4-chlorophenyl)-1-(1,2,3,6-tetrahydropyridinyl)]butyl}-1H-pyrrole;

2,5-dimethyl-1-{4-[4-(4-chlorophenyl)-1-(1,2,3,6-tetrahydropyridinyl)]butyl}-1H-pyrrole hydrochloride;

1-{4-[4-(4-chlorophenyl)-1-(1,2,3,6-tetrahydropyridinyl)]butyl}-1H-pyrrole;

1-{4-[4-(4-chlorophenyl)-1-(1,2,3,6-tetrahydropyridinyl)]butyl}-1H-pyrrole hydrochloride;

1-{4-[4-(4-chlorophenyl)-1-1(1,2,3,6-tetrahydropyridinyl)]butyl}-1H-trizole hydrochloride.

* * * * *